US010945663B2

(12) United States Patent
Bozkurt et al.

(10) Patent No.: US 10,945,663 B2
(45) Date of Patent: Mar. 16, 2021

(54) SMART SENSING SYSTEMS AND RELATED METHODS

(71) Applicant: North Carolina State University, Raleigh, NC (US)

(72) Inventors: Alper Bozkurt, Raleigh, NC (US); Tushar Ghosh, Raleigh, NC (US); Michael McKnight, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/518,712

(22) PCT Filed: Nov. 4, 2015

(86) PCT No.: PCT/US2015/059118
§ 371 (c)(1),
(2) Date: Apr. 12, 2017

(87) PCT Pub. No.: WO2016/073655
PCT Pub. Date: May 12, 2016

(65) Prior Publication Data
US 2017/0224280 A1  Aug. 10, 2017

Related U.S. Application Data

(60) Provisional application No. 62/244,523, filed on Oct. 21, 2015, provisional application No. 62/075,118, filed on Nov. 4, 2014.

(51) Int. Cl.
*A61B 5/04* (2006.01)
*A61B 5/00* (2006.01)
(Continued)

(52) U.S. Cl.
CPC ........ *A61B 5/6808* (2013.01); *A61B 5/02405* (2013.01); *A61B 5/0537* (2013.01);
(Continued)

(58) Field of Classification Search
CPC .... D03D 1/0088; H05K 1/038; H05K 1/0283; H05K 2201/0281; H05K 2201/029;
(Continued)

(56) References Cited

U.S. PATENT DOCUMENTS 6,210,771 B1 * 4/2001 Post .................... H05K 3/10
428/100
6,493,933 B1  12/2002 Post et al.
(Continued)

FOREIGN PATENT DOCUMENTS

WO  WO 2002/030279  4/2002
WO  WO 2007/050650  5/2007
(Continued)

OTHER PUBLICATIONS

Al-Saleh et al., "A review of vapor grown carbon nanofiber/polymer conductive composites," Carbon. 2009, 47(1), 2-22.
(Continued)

*Primary Examiner* — Joseph A Stoklosa
*Assistant Examiner* — Brian M Antiskay
(74) *Attorney, Agent, or Firm* — Michael Best & Friedrich LLP

(57) ABSTRACT

A smart patch including multi-component strands integrated into clothing or other textiles where the strands of the smart patch include sensory elements that can simultaneously measure tactile forces, moisture/wetness, and other signals, such as biopotentials. A sensing system comprising: a first set of strands including a plurality of first multi-component strands, each of the first multi-component strands including a conductive portion and a non-conductive portion; and a second set of strands including a plurality of second multi-component strands, each of the second multicomponent strands including a conductive portion and a non-conductive portion, and a plurality of third multi-component strands,
(Continued)

each of the third multicomponent strands including a conductive portion and a non-conductive portion, the third multi-component strands being different than the first multi-component strands and the second multi-component strands.

17 Claims, 25 Drawing Sheets

(51) Int. Cl.
| | |
|---|---|
| A61B 5/024 | (2006.01) |
| A61B 5/0537 | (2021.01) |
| A61B 5/08 | (2006.01) |
| A61B 5/11 | (2006.01) |
| A61B 5/20 | (2006.01) |
| A61F 13/42 | (2006.01) |
| G01N 27/04 | (2006.01) |
| F41H 1/02 | (2006.01) |
| G01L 1/14 | (2006.01) |
| G01L 1/20 | (2006.01) |
| D03D 11/00 | (2006.01) |
| D03D 1/00 | (2006.01) |
| D02G 3/44 | (2006.01) |
| D01D 5/253 | (2006.01) |
| A61B 5/282 | (2021.01) |
| G01L 5/00 | (2006.01) |
| A61F 13/08 | (2006.01) |

(52) U.S. Cl.
CPC .......... *A61B 5/0816* (2013.01); *A61B 5/1126* (2013.01); *A61B 5/208* (2013.01); *A61B 5/282* (2021.01); *A61B 5/6804* (2013.01); *A61F 13/42* (2013.01); *D01D 5/253* (2013.01); *D02G 3/441* (2013.01); *D03D 1/0088* (2013.01); *D03D 11/00* (2013.01); *F41H 1/02* (2013.01); *G01L 1/14* (2013.01); *G01L 1/205* (2013.01); *G01L 5/0014* (2013.01); *G01N 27/048* (2013.01); *A41D 2400/00* (2013.01); *A61B 2562/125* (2013.01); *A61F 13/08* (2013.01); *D10B 2401/18* (2013.01); *D10B 2403/02431* (2013.01)

(58) Field of Classification Search
CPC ... A61B 5/6804; A61B 5/6805; A61B 5/0205; A61B 5/1118; A61B 5/0402; D10B 2403/02431
USPC ....... 600/372, 382, 384, 386, 388–390, 393, 600/395; 607/115
See application file for complete search history.

(56) References Cited

U.S. PATENT DOCUMENTS

| | | | |
|---|---|---|---|
| 6,729,025 B2 | 5/2004 | Farrell et al. | |
| 6,852,395 B2 | 2/2005 | Dhawan et al. | |
| 7,329,323 B2 | 2/2008 | Dhawan et al. | |
| 7,348,285 B2 | 3/2008 | Dhawan et al. | |
| 7,828,019 B2* | 11/2010 | Shen .................... | A61B 5/6804 139/383 R |
| 7,845,022 B1* | 12/2010 | Surve ..................... | C23C 4/04 2/243.1 |
| 8,137,811 B2 | 3/2012 | Merchant et al. | |
| 8,171,755 B2* | 5/2012 | Jahn ........................ | D04B 1/16 66/170 |
| 8,298,968 B2* | 10/2012 | Swallow .............. | D03D 1/0088 345/173 |
| 8,800,386 B2 | 8/2014 | Taylor | |
| 8,897,888 B2* | 11/2014 | Parker ................ | A61M 25/0009 181/229 |
| 8,996,942 B2* | 3/2015 | Ellis ..................... | G11C 29/023 714/733 |
| 9,182,845 B2* | 11/2015 | Lussey ................ | G06F 3/0414 |
| 9,211,085 B2* | 12/2015 | Streeter .............. | A61B 5/0816 |
| 2003/0212319 A1 | 11/2003 | Magill | |
| 2007/0089800 A1 | 4/2007 | Sharma | |
| 2010/0198043 A1 | 8/2010 | Holzer et al. | |
| 2010/0234715 A1 | 9/2010 | Shin et al. | |
| 2011/0203390 A1* | 8/2011 | Tao ..................... | A43B 3/0005 73/862.046 |
| 2012/0190952 A1 | 7/2012 | Stafford | |
| 2014/0210036 A1 | 7/2014 | Sunier et al. | |
| 2014/0238151 A1 | 8/2014 | Dunne et al. | |

FOREIGN PATENT DOCUMENTS

| | | |
|---|---|---|
| WO | WO 2014/001577 | 1/2014 |
| WO | WO 2014/138204 | 9/2014 |

OTHER PUBLICATIONS

Arora et al., "Dielectric elastomer based prototype fiber actuators," Sensors and Actuators A—Physical, 2007, 136(1), 321-328.

Balberg, "Tunneling and nonuniversal conductivity in composite materials," Phys. Rev. Lett. 1987, 59(12), 1305-1308.

Barbaro et al., "Active Devices Based on Organic Semiconductors for Wearable Applications," IEEE Transactions on Information Technology in Biomedicine, 2010, 14(3), 758-766.

Beckmann et al., "Characterization of textile electrodes and conductors using standardized measurement setups," Physiol. Meas. 2010, 31(2), 233-247.

Bhattacharya et al., "Rechargeable electronic textile battery," Appl. Phys. Lett. 2009, 95(22), 223305.

Bonderover et al., "A woven inverter circuit for e-textile applications," IEEE Electron Device Lett 2004, 25(5), 295-297.

Bryning et al., "Very Low Conductivity Threshold in Bulk Isotropic Single-Walled Carbon Nanotube—Epoxy Composites," Advanced Materials, 2005, 17(9), 1186-1191.

Carpi et al., "Electroactive Polymer-Based Devices for e-Textiles in Biomedicine," IEEE Transactions on Information Technology in Biomedicine, 2005, vol. 9, No. 3, pp. 295-318.

Charalambides et al., "All-elastomer in-plane MEMS capacitive tactile sensor for normal force detection," in 2013 IEEE, 2013, No. 1, pp. 1-4.

Cheng et al., "Analysis of a concentric coplanar capacitor for epidermal hydration sensing" Sensors and Actuators A: Physical, 2013, 203, 149-153.

Cherenack et al., "Woven electronic fibers with sensing and display functions for smart textiles," Adv Mater. 2010, 22(45), 5178-5182.

Chuangchote et al., "Design of Metal Wires-based Organic Photovoltaic Cells," 9th Eco-Energy and Materials Science and Engineering Symposium. 2011, 9, 553-58.

Clerc et al., "Precise determination of the conductivity exponent of 3D percolation using exact numerical renormalization," The European Physical Journal B-Condensed Matter and Complex Systems. 2000, 15(3), 507-516.

Coosemans et al., "Integrating wireless ECG monitoring in textiles," Sensors and Actuators A-Physical. 2006, 130, 48-53.

De Jong et al., "Carbon Nanofibers: Catalytic Synthesis and Applications," Catalysis Reviews—Science and Engineering 2000, 42(4), 481-510.

De Rossi et al., "Dresswear: wearable hardware," Materials Science & Engineering C-Biomimetic and Supramolecular Systems. 1999, 7(1), 31-35.

De Rossi et al., "Electroactive Fabrics for Distributed, Conformable and Interactive Systems," IEEE, 2002, pp. 1608-1613.

De Rossi et al., "Monitoring body kinematics and gesture through sensing fabrics." Microtechnologies in Medicine and Biology, 1st Annual International, Conference On. 2000, 587-592.

De Rossi, "Electronic textiles: A logical step," Nature Materials, 2007, 6(5), 328-329.

(56) References Cited

OTHER PUBLICATIONS

Ding et al., "A simple, low waste and versatile procedure to make polymer electrochromic devices ," Journal of Materials Chemistry, 2011, 21(32), 11873-11878.
Dufour et al., "Electrowetting on functional fibers," Soft Matter, 2013, 9(2), 492-497.
Dutta, "Onviscosity—melt flow index relationship," Rheologica Acta, 1984, 23(5), 565-569.
El-Shiekh et al., "The Mechanics of Bicomponent Fibers, Part I : Theoretical Analysis," Text. Res. J. 1971, 41(4), 281-297.
Everage, "Theory of Stratified Bicomponent Flow of Polymer Melts. II. Interface Motion in Transient Flow," Transactions of the Society of Rheology, 1975, 19(4), 509-522.
Finni et al., "Measurement of EMG activity with textile electrodes embedded into clothing," Physiol. Meas, 2007, 28(11), 1405-1419.
Flandin et al., "Anomalous percolation transition in carbon-black—epoxy composite materials," Physical Review B, 1999, 59(22), 14349-14355.
Fouke et al., "Sensor for Measuring Surface Fluid Conductivity In Vivo," IEEE Trans. Biomed. Eng., 1988, vol. 35, No. 8822622, pp. 877-881.
Gao et al., "Sensors: Glass Fibers with Carbon Nanotube Networks as Multifunctional Sensors," Advanced Functional Materials, 2010, 20(12), 1885-1893.
Geng et al., "Effects of surfactant treatment on mechanical and electrical properties of CNT/epoxy nanocomposites," Composites Part A—Applied Science and Manufacturing, 2008, 39(12), 1876-1883.
Gorgutsa et al., "A woven 2D touchpad sensor and a 1D slide sensor using soft capacitor fibers," Smart Materials & Structures, 2012, 21(1), 015010.
Grajales et al., "Wearable multisensor heart rate monitor," Proc. 3th Int. Workshop on Wearable and Implantable Body Sensor Networks, Boston, 2006, 1-4.
Grillet et al., "Optical fiber sensors embedded into medical textiles for healthcare monitoring," IEEE Sensors Journal, 2008, 8(7-8), 1215-1222.
Gu et al., "A fully woven touchpad sensor based on soft capacitor fibers," 2011, 19 pages.
Gu et al., "Soft capacitor fibers for electronic textiles," Appl. Phys. Lett, 2010, 97(13), 133305.
Gu et al., "Soft capacitor fibers using conductive polymers for electronic textiles," Smart Materials & Structures, 2010, 19(11), 115006.
Hamedi et al., "Fibre-Embedded Electrolyte-Gated Field-Effect Transistors for e-Textiles," Adv Mater., 2009, 21(5), 573-577.
Hamedi et al., "Towards woven logic from organic electronic fibres," Nature Materials, 2007, 6(5), 357-362.
Han et al., "Copper oxide resistive switching memory for e-textile," Aip Advances, 2011, 1(3), 032162.
Han, "A study of coextrusion in a circular die," J Appl Polym Sci., 1975, 19(7), 1875-1883.
Hasegawa et al., "Fabrication of a wearable fabric tactile sensor produced by artificial hollow fiber," J. Micromechanics Microengineering, 2008, vol. 18, No. 085014, 8 pages.
Hong et al., "Effects of oxidative conditions on properties of multi-walled carbon nanotubes in polymer nanocomposites," Composites Sci. Technol., 2007, 67(6), 1027-1034.
Hou et al., "Flexible conductive threads for wearable dye-sensitized solar cells," Journal of Materials Chemistry, 2012, 22(14), 6549-6552.
Huang et al., "Epidermal impedance sensing sheets for precision hydration assessment and spatial mapping," IEEE Trans Biomed Eng., 2013, 60(10):2848-57.
Hwang et al., "A Polymer-based Flexible Tactile Sensor for Both Normal and Shear Load Detections and Its Application for Robotics," IEEE MEMS, 2007, pp. 556-563.
Ishijima, "Cardiopulmonary monitoring by textile electrodes without subject-awareness of being monitored," Med. Biol. Eng. Comput., 1997, 35(6), 685-690.
Jafari et al., "Adaptive and fault tolerant medical vest for life-critical medical monitoring." Proceedings of the 2005 ACM symposium on Applied computing, ACM, 2005, 272-279.
Jeevananda et al., "Investigation of multi-walled carbon nanotube-reinforced high-density polyethylene/carbon black nanocomposites using electrical, DSC and positron lifetime spectroscopy techniques," Polym. Int., 2009, 58(7), 775-780.
Jeevananda et al., "Polyaniline-multiwalled carbon nanotube composites: Characterization by WAXS and TGA," J Appl Polym Sci., 2008, 109(1), 200-210.
Jeffries, Bicomponent fibres, Watford, Merrow Publishing Co. Ltd, 1971.
Jiang et al., "Electrical and mechanical properties of polyimide—carbon nanotubes composites fabricated by in situ polymerization," Polymer, 2005, 46(18), 7418-7424.
Johnson et al., "Development of an integrated fluid sensor," IEEE Wescon/97 Conference Proceedings, 1997, pp. 495-500.
Kannaian et al., "Design and development of embroidered textile electrodes for continuous measurement of electrocardiogram signals," Journal of Industrial Textiles, 2013, 42(3), 303-318.
Kikutani et al., "Fiber Structure Formation in High-Speed Melt Spinning of Sheath-Core Type Bicomponent Fibers," FIBER, 1995, 51, 408-415.
Kikutani et al., "High-speed melt spinning of bicomponent fibers: Mechanism of fiber structure development in poly(ethylene terephthalate)/polypropylene system," J Appl Polym Sci., 1996, 62(11), 1913-1924.
Kim et al., "Influence of contact pressure and moisture on the signal quality of a newly developed textile ECG sensor shirt," Medical Devices and Biosensors, 2008. ISSS-MDBS 2008. 5th International Summer School and Symposium on 2008.
Kim et al., "Miniature electrocardiography sensor using a flexible printed circuit and MEMS technology," Proceedings of IEEE International Conference on Multisensor Fusion and Integration for Intelligent Systems, 2008, No. 1, pp. 545-550.
Koerner et al., "Deformation—morphology correlations in electrically conductive carbon nanotube—thermoplastic polyurethane nanocomposites," Polymer, 2005, 46(12), 4405-4420.
Laforgue et al., "Multifunctional resistive-heating and color-changing monofilaments produced by a single-step coaxial melt-spinning process," ACS Applied Materials & Interfaces, 2012, 4(6), 3163-3168.
Lee et al., "A flexible polymer tactile sensor: Fabrication and modular expandability for large area deployment," J Microelectromech Syst., 2006, 15(6), 1681-1686.
Lee et al., "Weave patterned organic transistors on fiber for E-textiles," IEEE Trans. Electron Devices, 2005, 52(2), 269-275.
Lee et al., "A Capacitive Proximity Sensor in Dual Implementation with Tactile Imaging Capability on a Single Flexible Platform for Robot Assistant Applications," 19th IEEE International Conference on MEMS, 2006, pp. 606-609.
Lewin M, Preston J (eds) High Technology Fibers, Part D: Bicomponent fibers. Marcel Dekker Inc, NY. 1996.
Li et al., "Effects of carbon blacks with various structures on vulcanization and reinforcement of filled ethylene-propylene-diene rubber," J. Electrostatics, 2009, 67(1), 73-75.
Li et al., "Performance of Electromyography Recorded Using Textile Electrodes in Classifying Arm Movements," Conf Proc IEEE Eng Med Biol Soc., 2011, 4243-6.
Liang et al., "Aggregate structure and percolation behavior in polymer/carbon black conductive composites," J. Appl. Phys., 2007, 102(8), 083508.
Lifton et al., "Preparation and electrowetting transitions on superhydrophobic/ hydrophilic bi-layer structures," Journal of Porous Materials, 2011, 18(5), 535-544.
Lin et al., "Microfabricated Impedance Sensors for Concurrent Tactile, Biopotential, and Wetness Detection," IEEE, 2014, 4 pages.
Linz et al., "Contactless EMG sensors embroidered onto textile," 4th International Workshop on Wearable and Implantable Body Sensor Networks, 2007, pp. 29-34.

(56) References Cited

OTHER PUBLICATIONS

Liu et al., "One-Step Ionic-Liquid-Assited Electrochemical Synthesis of Ionic-Liquid-Functionalized Graphene Sheets Directly from Graphite," J. Chen, Advanced Functional Materials, 2008, 18(10), 1518-1525.
Lofhede et al., "Textile electrodes for EEG recording a pilot study," Sensors, 2012, 12(12), 16907-16919.
Lofhede et al., "Soft textile electrodes for EEG monitoring," presented at Information Technology and Applications in Biomedicine (ITAB), 2010 10th IEEE International Conference.
Loos et al., "Visualization of single-wall carbon nanotube (SWNT) networks in conductive polystyrene nanocomposites by charge contrast imaging," Ultramicroscopy, 2005, 104(2), 160-167.
Maccioni et al., "Towards the textile transistor: Assembly and characterization of an organic field effect transistor with a cylindrical geometry," Appl. Phys. Lett, 2006, 89(14), 143515.
MacLean, "A Theoretical Analysis of Bicomponent Flow and the Problem of Interface Shape," Transactions of the Society of Rheology, 1973, 17(3), 385-399.
Marculescu et al., "Electronic textiles: A platform for pervasive computing" Proc IEEE, 2003, 91(12), 1995-2018.
Marquez et al., "Textile electrodes in Electrical Bioimpedance measurements—a comparison with conventional Ag/AgC1 electrodes," Conference proceedings : Annual International Conference of the IEEE Engineering in Medicine and Biology Society, IEEE Engineering in Medicine and Biology Society, Conference. 2009, 2009, 4816-9.
Martin et al., "Formation of percolating networks in multi-wall carbon-nanotube-epoxy composites," Composites Sci. Technol, 2004, 64(15), 2309-2316.
Martinez et al., "Diagnostics for the developing world: Microfluidic paper-based analytical devices," Anal. Chem., vol. 82, No. 1, 2010, pp. 3-10.
Martinez et al., "Patterned paper as a platform for inexpensive, low-volume, portable bioassays," Angew. Chemie Int. Ed., vol. 46, 2007, pp. 1318-1320.
Mattmann et al., "Sensor for Measuring Strain in Textile," Sensors, 2008, 8(6), 3719-3732.
McCall et al., "Underpotential Deposition on Alloys," J. Electrochem. Soc., 2001, 148(6), E290-E293.
McKnight et al., "Towards paper based diaper sensors," Biomedical Circuits and Systems Conference (BioCAS), IEEE 2015, Atlanta, GA, pp. 1-4.
Meredith et al., "New MEMS Technologies for Integrated Vehicle Health Management and Fluid Sensing Applications," in 2008 IEEE Aerospace conference Proceedings.
Mestrovic et al., "Preliminary study of dry knitted fabric electrodes for physiological monitoring," IEEE, 2007, 601-606.
Moskalyuk et al., "Electrical conductivity of polypropylene fibers with dispersed carbon fillers," Physics of the Solid State, 2012, 54(10), 2122-2127.
Mostafalu et al., "Wireless Flexible Smart Bandage for Continuous Monitoring of Wound Oxygenation," IEEE, 2015, vol. 9, No. 5, 670-677.
Mugele et al., "Electrowetting: frombasics to applications," Journal of Physics: Condensed Matter, 2005, 17(28), R705.
Najafi et al., "Radiation resistant polymer—carbon nanotube nanocomposite thin films," Colloids Surf. Physicochem. Eng. Aspects, 2005, 257, 333-337.
Nakano et al., "Resistivity—temperature characteristics of filler-dispersed polymer composites," Polymer, 2012, 53(26), 6112-6117.
Nam et al., "High-Performance Low-Voltage Organic Field-Effect Transistors Prepared on Electro-Polished Aluminum Wires," ACS Applied Materials & Interfaces, 2012, 4(1), 6-10.
Nie et al., "Electrochemical sensing in paper-based microfluidic devices.," Lab Chip, 2010, vol. 10, No. c, pp. 477-483.
O'Connor et al., "Fiber based organic photovoltaic devices," Appl. Phys. Lett., 2008, 92(19), 193306.
O'Connor et al., "Fiber Shaped Organic Light Emitting Device," Adv Mater., 2007, 19(22), 3897-3900.
Park et al., "An improved algorithm for respiration signal extraction from electrocardiogram measured by conductive textile electrodes using instantaneous frequency estimation," Med. Biol. Eng. Comput., 2008, 46(2), 147-158.
Park et al., "Effects of surface modification on the dispersion and electrical conductivity of carbon nanotube/polyaniline composites," Scr. Mater., 2009, 60(7), 551-554.
Parkova et al., "Integration of Flexible Keypad into Clothing," presented at Proceedings of the 8th International Scientific and Practical Conference "Environment. Technology. Resources."—Rezekne 2011, 173-180.
Peltokangas et al., "Night-Time EKG and HRV Monitoring With Bed Sheet Integrated Textile Electrodes ," IEEE Transactions on Information Technology in Biomedicine, 2012, 16(5), 935-942.
Pereira et al., "Textile moisture sensor matrix for monitoring of disabled and bed-rest patients," in IEEE EUROCON-International Conference on Computer as a Tool (EUROCON), Apr. 2011, 1-4.
Pfeifer et al., "Analysis of electrical percolation thresholds in carbon nanotube networks using the Weibull probability distribution," J. Appl. Phys., 2010, 108(2), 024305.
Post et al., "E-broidery: Design and fabrication of textile-based computing," IBM Syst J., 2000, 39(3-4), 840-860.
Radhakrishnan et al., "High-Speed Melt Spinning of Sheath-Core Bicomponent Polyester Fibers: High and Low Molecular Weight Poly(ethylene Terephthalate) Systems ," Text. Res. J., 1997, 67(9), 684-694.
Rahimi et al., "Flexible Sensors for Chronic Wound Management," IEEE Reviews in Biomedical Engineering,. 2014, vol. 7, pp. 73-86.
Rattfaelt et al., "Electrical characteristics of conductive yarns and textile electrodes for medical applications," Med. Biol. Eng. Comput., 2007, 45(12), 1251-1257.
Riistama et al., Conference proceedings: Annual International Conference of the IEEE Engineering in Medicine and Biology Society, IEEE Engineering in Medicine and Biology Society, Conference, 2006, 1, 6021-4.
Rohlfing et al., "What's Happening in the Melt-Flow Plastometer: The Role of Elongational Viscosity," Technical papers of the Annual Technical Conference-Society of Plastics Engineers Incorporated 1997, vol. 1, pp. 1010-1014.
Rothmaier et al., "Textile Pressure Sensor Made of Flexible Plastic Optical Fibers," Sensors, 2008, 8(7), 4318-4329.
Rul et al., "Percolation of single-walled carbon nanotubes in ceramic matrix nanocomposites," Acta Materialia., 2004, 52(4), 1061-1067.
Sahimi, Heterogeneous Materials: Linear transport and optical properties, vol. 22, Springer Verlag 2003.
Sahimi, M. Flow and Transport in Porous Media and Fractured Rock 12, VCH, Weinheim, Germany,1995.
Salvo et al., "A Wearable Sensor for Measuring Sweat Rate," IEEE Sensors Journal, 2010, vol. 10, No. 10, pp. 1557-1558.
Scilingo et al., "Performance evaluation of sensing fabrics for monitoring physiological and biomechanical variables," IEEE Transactions on Information Technology in Biomedicine, 2005, 9(3), 345-352.
Searle et al., "A direct comparison of wet, dry and insulating bioelectric recording electrodes," Physiol. Meas., 2000, 21(2), 271-283.
Seavey et al., "Quantifying Relationships among the Molecular Weight Distribution, Non-Newtonian Shear Viscosity, and Melt Index for Linear Polymers," Ind Eng Chem Res., 2003, 42(21), 5354-5362.
Sergio et al., "A dynamically reconfigurable monolithic CMOS pressure sensor for smart fabric," IEEE J Solid State Circuits, 2003, 38(6), 966-975.
Sergio et al., "A Textile Based Capacitive Pressure Sensor," in Proceedings of IEEE Sensors, 2002, pp. 1625-1630.
Service, "Technology. Electronic textiles charge ahead," Science, 2003, 301(5635), 909-11.
Shen et al., "Synthesis of polystyrene-carbon nanofibers nanocomposite foams," Polymer, 2005, 46(14), 5218-5224.
Sheng et al., "Fluctuation-induced tunneling conduction in carbon-polyvinylchloride composites," Phys. Rev. Lett, 1978, 40(18), 1197-1200.

(56) References Cited

OTHER PUBLICATIONS

Shenoy et al., "From melt flow index to rheogram," Rheologica Acta, 1983, 22(1), 90-101.
Siegel et al., "Foldable printed circuit boards on paper substrates," Adv. Funct. Mater., 2010, vol. 20, pp. 28-35.
Song et al., "Influence of dispersion state of carbon nanotubes on physical properties of epoxy nanocomposites," Carbon, 2005, 43(7), 1378-1385.
Southern et al., "Additional observations on stratified bicomponent flow of polymer melts in a tube," Journal of Polymer Science Part B—Polymer Physics, 1975, 13(4), 863-869.
Spitalsky et al., "Carbon nanotube—polymer composites: chemistry, processing, mechanical and electrical properties," Progress in Polymer Science, 2010, 35(3), 357-401.
Spontak et al., "Thermoplastic elastomers: fundamentals and applications," Current Opinion in Colloid & Interface. Science, 2000, 5(5-6), 334-341.
Stauffer, D. & Aharony, A. Introduction to Percolation Theory, Taylor and Francis, London 1985.
Strumpler et al., "Conducting Polymer Composites," Journal of Electroceramics, 1999, 3(4), 329-346.
Tao et al., "Geometry pattern for the wire organic electrochemical textile transistor," J. Electrochem. Soc., 2011, 158(5), H572-H577.
Tao et al., "Real-time performance of textile electrodes in electromyogram pattern-recognition based prosthesis control", presented at Biomedical and Health Informatics (BHI), IEEE, 2012, 487-490.
Tarabella et al., "A single cotton fiber organic electrochemical transistor for liquid electrolyte saline sensing" Journal of Materials Chemistry, 2012, 22(45), 23830-23834.
Toprakci et al., "Polymer Nanocomposites Containing Carbon Nanofibers as Soft Printable Sensors Exhibiting Strain-Reversible Piezoresistivity," Adv. Funct. Mater., 23, 2013, 5536.
Uhland, "Stratified two-phase flog of molten polymers in circular dies," Polymer Engineering & Science, 1977, 17(9), 671-681.
Verplanck et al., "Wettability switching techniques on superhydrophobic surfaces," Nanoscale Research Letters, 2007, 2(12), 577-596.
Vervust et al., "Integration of stretchable and washable electronic modules for smart textile applications," Journal of the Textile Institute, 2012, 103(10), 1127-1138.
White et al., "Theory of Interface Distortion in Stratified Two-Phase Flow," Transactions of the Society of Rheology, 1975, 19(3), 457-479.
White et al., "The influence of carbon black on the extrusion characteristics and rheological properties of elastomers: Polybutadiene and butadiene—styrene copolymer," J Appl Polym Sci., 2003, 18(4), 1013-1038.
Wilkie, "New products from bicomponents," Int Nonwovens Journal, 1999, 8 (1): 146-151.
Yagi et al., "Multistage stretching of high-density polyethylene monofilaments in melt spinning," J Appl Polym Sci., 1978, 22(9), 2553-2571.
Youngs, "Exploring the universal nature of electrical percolation exponents by genetic algorithm fitting with general effective medium theory," Journal of Physics D—Applied Physics, 2002, 35(23), 3127-3137.
Yue et al., "Polypyrrole coated nylon Lycra fabric as stretchable electrode for supercapacitor applications," Electrochim. Acta., 2012, 68, 18-24.
Zhang et al., "A low-power ECoG/EEG processing IC with integrated multiband energy extractor," IEEE Transactions on Circuits and Systems I: Regular Papers, 58(9), 2069-2082.
Zhang et al., "Preparation and characterization of gas-sensitive composites from multi-walled carbon nanotubes/polystyrene," Sensors and Actuators B—Chemical. 2005, 109(2), 323-328.
Ziabicki, Fundamentals of fibre formation: the science of fibre spinning and drawing, Wiley, London;New York 1976.
International Search Report and Written Opinion for Application No. PCT/US2015/059118 dated May 16, 2016 (21 pages).

\* cited by examiner

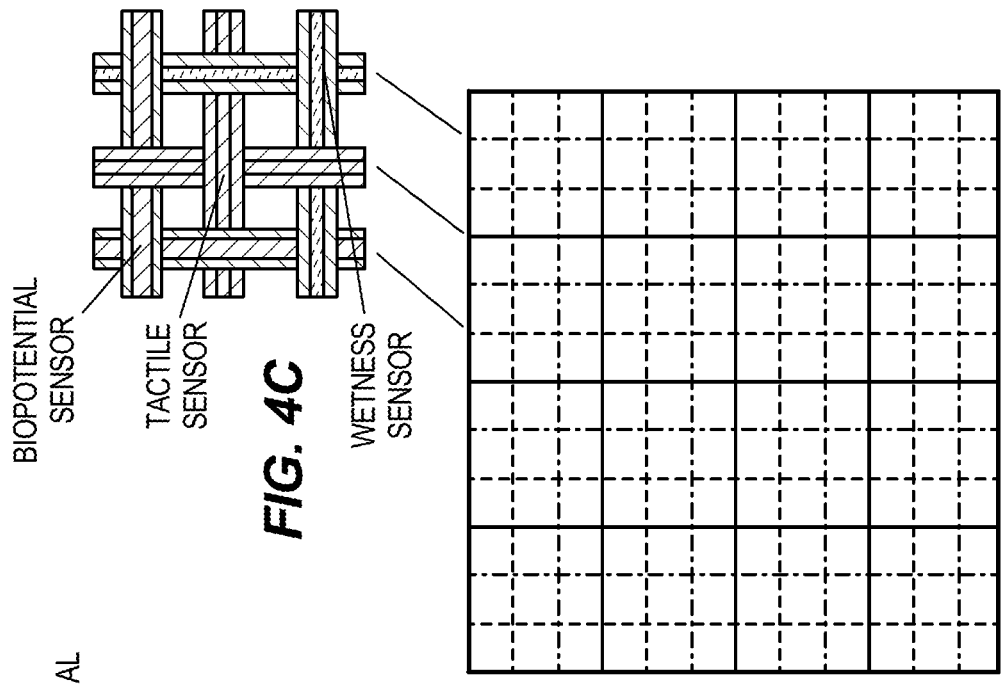
FIG. 4C
FIG. 4D
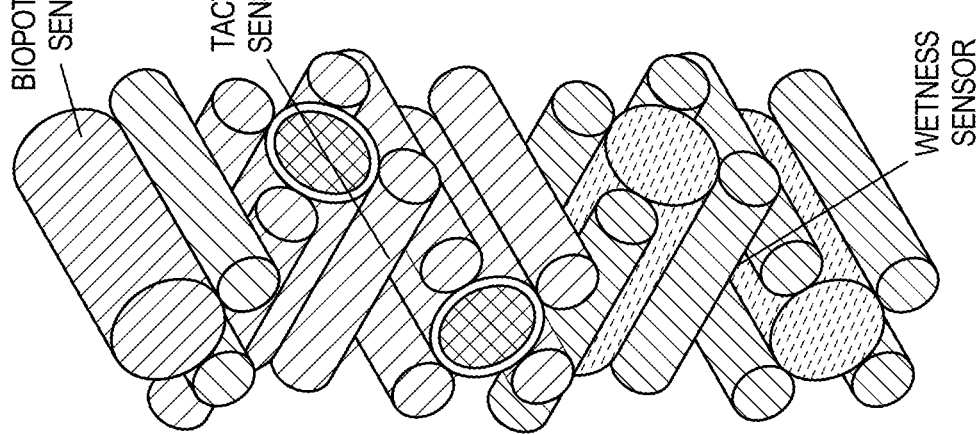
FIG. 4B
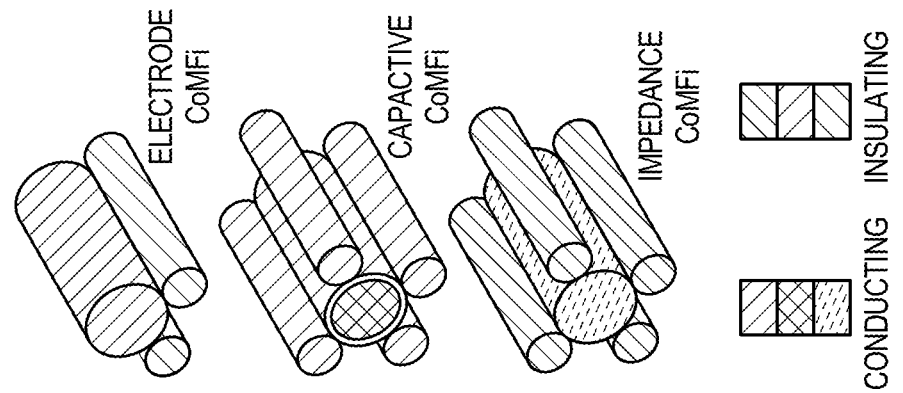
FIG. 4A

| Dimension | Size (in mm) |
|---|---|
| A1, A2 | 1 |
| B | 1 |
| C | 1.5 |
| D | 3 |

| Layer | Thickness (in mm) |
|---|---|
| Conductive (E) | 0.2 |
| Insulator (F) | 1 |

| Dimension | Size (in μm) |
|---|---|
| A1, A2 | 150 |
| B | 50 |
| C | 150 |
| D | 350 |

| Layer | Thickness (in μm) |
|---|---|
| Conductive (E) | 0.2 |
| Inner Insulator (F) | 1-2 |
| Outer Insulator (G) | 12-13 |

| Dimension | Size (in um) |
|---|---|
| A1, A2 | 250 |
| B | 250 |
| C | 750 |

| Layer | Approximate Thickness (in um) |
|---|---|
| Conductive | 400 |
| Insulating | 800 |

| | CONDUCTIVE (SILVER/SILVER-CHLORIDE PASTE) |
| | INSULATING (CLEANROOM PAPER) |

| DIMENSION | SIZE (IN um) |
|---|---|
| A1, A2 | 100 |
| B | 200-250 |
| C | 400-450 |

| LAYER | THICKNESS (IN um) |
|---|---|
| CONDUCTIVE (E) | 0.2-0.4 |
| INNER INSULATOR (F) | 70-90 |
| OUTER INSULATOR (G) | 200-250 |

SMART SENSING SYSTEMS AND RELATED METHODS

RELATED APPLICATIONS

This application is a national stage filing under 35 U.S.C. § 371 of International Application No. PCT/US2015/059118, filed on Nov. 4, 2015, which claims the benefit of priority to U.S. Provisional Application No. 62/075,118 filed on Nov. 4, 2014 and to U.S. Provisional Application No. 62/244,523 filed on Oct. 21, 2015. The contents of these applications are incorporated herein by reference.

STATEMENT REGARDING FEDERALLY SPONSORED RESEARCH OR DEVELOPMENT

This invention was made with government support under grant numbers 1252376 and 1509043 awarded by the National Science Foundation. The government has certain rights in the invention.

BACKGROUND OF THE INVENTION

The success of electronic textile (e-textile) efforts requires the ability to (i) integrate various electronic functionalities into textiles in a truly unobtrusive manner and (ii) preserve the unique and essential "textile" characteristics (strength, flexibility, texture, softness, porosity, comfort, and stability (environmental and in-use)) of fibrous structures. In the textile hierarchy, fibers are used to form yarns, and yarns are woven into fabrics. The sensory patches of the present invention are created from monofilament yarns or fibers. For purposes of reviewing the state of the art, there is no distinction between fibers and monofilament yarns.

Electronic Textiles: Integration of electronic sensing systems and textiles has, for the most part, been external, in which conventional semiconductor-based off-the-shelf rigid devices/modules have been embedded into yarn, fiber, or fabrics [B Farrell, P W Nguyen, J Teverovsky, J Slade, M Powell, U.S. Pat. No. 6,729,025, 2004; E. R. Post, N. Gershenfeld, U.S. Pat. No. 6,493,933, 2002; T. Vervust, G. Buyle, F. Bossuyt, J. Vanfleteren, Journal of the Textile Institute. 2012, 103(10), 1127-1138; Jafari, Roozbeh, Foad Dabiri, Philip Brisk, and Majid Sarrafzadeh. "Adaptive and fault tolerant medical vest for life-critical medical monitoring." In Proceedings of the 2005 ACM symposium on Applied computing, ACM, 2005, 272-279]. From a practical standpoint a key step for the integration of truly mass-produced e-textile based sensor systems should be to incorporate electronic sensor fabrication within the textile production. Accordingly, in an integral approach, the constituents (e.g., fibers or yarns) of a textile product are directly fashioned into electrical devices by incorporating appropriate functional design and materials. These include "fiber"-shaped photovoltaic devices [S. Chuangchote, T. Sagawa, S. Yoshikawa, 9th Eco-Energy and Materials Science and Engineering Symposium. 2011, 9, 553-58; O'Connor, K. P. Pipe, M. Shtein, Appl. Phys. Lett. 2008, 92(19), 193306; S. Hou, Z. Lv, H. Wu, X. Cai, Z. Chu, Yiliguma, D. Zou, Journal of Materials Chemistry. 2012, 22(14), 6549-6552], transistors [M. Hamedi, L. Herlogsson, X. Crispin, R. Marcilla, M. Berggren, O. Inganas, Adv Mater. 2009, 21(5), 573; X. Tao, V. Koncar, C. Dufour, J. Electrochem. Soc. 2011, 158(5), H572-H577; S. Nam, J. Jang, J. Park, S. W. Kim, C. E. Park, J. M. Kim, Acs Applied Materials & Interfaces. 2012, 4(1), 6-10; M. Hamedi, R. Forchheimer, O. Inganas, Nature Materials. 2007, 6(5), 357-362; De Rossi, Nature Materials. 2007, 6(5), 328-329; J. Lee, V. Subramanian, IEEE Trans. Electron Devices. 2005, 52(2), 269-275; M. Maccioni, E. Orgiu, P. Cosseddu, S. Locci, A. Bonfiglio, Appl. Phys. Lett. 2006, 89(14), 143515], logic circuits [Bonderover, S. Wagner, IEEE Electron Device Lett. 2004, 25(5), 295-297], sensors [S. Gao, R. Zhuang, J. Zhang, J. Liu, E. Maeder, Advanced Functional Materials. 2010, 20(12), 1885-1893; G. Tarabella, M. Villani, D. Calestani, R. Mosca, S. Iannotta, A. Zappettini, N. Coppede, Journal of Materials Chemistry. 2012, 22(45), 23830-23834], actuators [S. Arora, T. Ghosh, J. Muth, Sensors and Actuators A-Physical. 2007, 136(1), 321-328], other electronic/optical devices [O'Connor, K. H. An, Y. Zhao, K. P. Pipe, M. Shtein, Adv Mater. 2007, 19(22), 3897-3900; Laforgue, G. Rouget, S. Dubost, M. F. Champagne, L. Robitaille, Acs Applied Materials & Interfaces. 2012, 4(6), 3163-3168; J. F. Gu, S. Gorgutsa, M. Skorobogatiy, Smart Materials & Structures. 2010, 19(11), 115006] in addition to "fabric" based devices [R. Bhattacharya, M. M. de Kok, J. Zhou, Appl. Phys. Lett. 2009, 95(22), 223305; Yue, C. Wang, X. Ding, G. G. Wallace, Electrochim. Acta. 2012, 68, 18-24; J. Han, M. Meyyappan, Aip Advances. 2011, 1(3), 032162; Y. Ding, M. A. Invernale, D. M. D. Mamangun, A. Kumar, G. A. Sotzing, Journal of Materials Chemistry. 2011, 21(32), 11873-11878; M. Barbaro, A. Caboni, P. Cosseddu, G. Mattana, A. Bonfiglio, IEEE Transactions on Information Technology in Biomedicine. 2010, 14(3), 758-766; De Rossi, A. Della Santa, A. Mazzoldi, Materials Science & Engineering C-Biomimetic and Supramolecular Systems. 1999, 7(1), 31-35; De Rossi, D., F. Lorussi, A. Mazzoldi, E. P. Scilingo, and W. Rocchia, "Strain amplified electroactive conducting polymer actuator," In Proceedings of SPIE, vol. 4329. 2001; De Rossi, D., A. Mazzoldi, A. Dittmar, and L. Schwenzfeier, "Dresswear: Smart fabrics and interactive clothing." In: 4th workshop on multifunctional & smart polymer systems, Dublin, Ireland, 20-23; De Rossi, D., F. Lorussi, A. Mazzoldi, P. Orsini, and E. P. Scilingo. "Monitoring body kinematics and gesture through sensing fabrics." In Microtechnologies in Medicine and Biology, 1st Annual International, Conference On. 2000, 587-592]. However, some of the e-textile device fabrication reported in the literature use complex direct patterning on fibers that may not render themselves to textile-compatible manufacturing [S. Chuangchote, T. Sagawa, S. Yoshikawa, 9th Eco-Energy and Materials Science and Engineering Symposium. 2011, 9, 553-58; O'Connor, K. P. Pipe, M. Shtein, Appl. Phys. Lett. 2008, 92(19), 193306; S. Hou, Z. Lv, H. Wu, X. Cai, Z. Chu, Yiliguma, D. Zou, Journal of Materials Chemistry. 2012, 22(14), 6549-6552; M. Hamedi, L. Herlogsson, X. Crispin, R. Marcilla, M. Berggren, O. Inganas, Adv Mater. 2009, 21(5), 573; X. Tao, V. Koncar, C. Dufour, J. Electrochem. Soc. 2011, 158(5), H572-H577; S. Nam, J. Jang, J. Park, S. W. Kim, C. E. Park, J. M. Kim, Acs Applied Materials & Interfaces. 2012, 4(1), 6-10; J. Lee, V. Subramanian, IEEE Trans. Electron Devices. 2005, 52(2), 269-275; M. Maccioni, E. Orgiu, P. Cosseddu, S. Locci, A. Bonfiglio, Appl. Phys. Lett. 2006, 89(14), 143515; Bonderover, S. Wagner, IEEE Electron Device Lett. 2004, 25(5), 295-297]. Some of the obvious advantages of organic electronic materials, such as mechanical flexibility and therefore compatibility with textile-fiber-forming polymers, over their inorganic counterparts must be considered in choosing materials for e-textiles.

Multicomponent fibers: In co-extruded multicomponent fiber (CoMFi) extrusion, polymers of different chemical and/or physical properties are melt-extruded from the same spinneret, with various cross-sectional arrangements defined by the engineered extrusion die or nozzle. These multicomponent fibers synergistically combine the properties of two or more individual polymers into one fiber with precise and distinct segments of each polymer type along its length. Early efforts to develop multicomponent fibers were focused primarily on achieving crimp and therefore bulk (or loft) and stretch in manmade fibers [Cooke T F In: Lewin M, Preston J (eds) High Technology Fibers, Part D: Bicomponent fibers. Marcel Dekker Inc, NY. 1996; Elshiekh, J. Bogdan N, R. Gupta, Text. Res. J. 1971, 41(4), 281-297]. The most common variety of CoMFi is the sheath-core type bicomponent fiber that are made up of two polymer components in such a way that one polymer (core) is fully surrounded by another polymer (sheath) (FIG. 1). The applications include, but are not limited to, specialty fibers for thermal bonding in nonwovens [Cooke T F In: Lewin M, Preston J (eds) High Technology Fibers, Part D: Bicomponent fibers. Marcel Dekker Inc, NY. 1996; Elshiekh, J. Bogdan N, R. Gupta, Text. Res. J. 1971, 41(4), 281-297; Wilkie A E, New products from bicomponents. Int Nonwovens J. 1999, 8 (1): 146-151; R. Jeffries 1929-, Bicomponent fibres, Watford, Merrow Publishing Co. Ltd, 1971], and surface property enhancement [Wilkie A E, New products from bicomponents. Int Nonwovens J. 1999, 8 (1): 146-151]. Cross-sectional shapes of some of the other common varieties of bicomponent fibers include side-by-side, segmented-pie, tipped trilobal and islands-in-the sea (FIG. 1) [N. Fedorova, Investigation of the utility of islands-in-the-sea bicomponent fiber technology in the spunbond process. PhD Thesis NC State University, 2006]. The knowledge of "tessellation" can be used to form different cross-section structures where the flat planes are tiled using one or more geometric shapes with no overlaps and no gaps. The concept of combining multiple polymers into a single fiber with various cross-sectional dispositions is enticing for e-textile applications. However, there are some limitations on the combinations of materials that may be used in a CoMFi. The thermal and stress histories experienced by the polymers coextruded to form a single filament are critical. The relative differences in the inherent polymer characteristics, such as, thermal behavior and viscosity are found to be some of the major factors influencing the mutual interaction between the component polymers. Significant difference in these characteristics may result in differing elongational stress development and thereby the orientation and orientation-induced crystallization development in the components [T. Kikutani, S. Arikawa, A. Takaku, N. Okui, FIBER. 1995, 51, 408-415; T. Kikutani, J. Radhakrishnan, S. Arikawa, A. Takaku, N. Okui, X. Jin, F. Niwa, Y. Kudo, J Appl Polym Sci. 1996, 62(11), 1913-1924; J. Radhakrishnan, T. Kikutani, N. Okui, Text. Res. J. 1997, 67(9), 684-694. 78]. Large differences in viscosity between the polymers can complicate the production of the desired cross-section, and in extreme cases make the system unspinnable. If a splitable fiber is not the end goal, the component polymers must also be sufficiently compatible at the interface so as to have adequate interfacial adhesion [Han, J Appl Polym Sci. 1975, 19(7), 1875-1883; J. Southern, R. Ballman, Journal of Polymer Science Part B-Polymer Physics. 1975, 13(4), 863-869; Everage, Transactions of the Society of Rheology. 1975, 19(4), 509-522]. The phenomenon of interface movement leading to the encapsulation of more viscous component has been explained by the concept of minimum viscous dissipation. Numerical simulations have been used to show that as the two polymers traverse the capillary, they spontaneously rearrange themselves until the configuration which produces the least resistance to flow is obtained. Thus, the material with lower viscosity moves to the regions of greater shear, near the walls, leading to the encapsulation effect [J. L. White, B. Lee, Transactions of the Society of Rheology. 1975, 19(3), 457-479; Uhland, Polymer Engineering & Science. 1977, 17(9), 671-681; L. MacLean, Transactions of the Society of Rheology. 1973, 17(3), 385-399]. In addition to viscosity, fiber properties in melt-extrusion are also determined by how the polymers behave in the quench and draw zones [Ziabicki, Fundamentals of fibre formation: the science of fibre spinning and drawing, Wiley, London; New York 1976; K. Yagi, C. Han, J Appl Polym Sci. 1978, 22(9), 2553-2571]. Therefore, not only the viscosities have to allow fiber formation, the quenching of the fibers determines if the ultimate fiber retains its shape and form after leaving the spinneret. Therefore, materials selection, processing, and structural design are keys to the success of the "Fiber IntegRated Sensor Technologies (FIRST)."

E-Textile based Biomedical and Environmental Sensing: Integrating sensors into textiles is a growing area of research [Service, R. F. (2003). Technology. Electronic textiles charge ahead. Science (New York, N.Y.), 301(5635), 909; Marculescu, R. Marculescu, N. Zamora, P. Stanley-Marbell, P. Khosla, S. Park, S. Jayaraman, S. Jung, C. Lauterbach, W. Weber, T. Kirstein, D. Cottet, J. Grzyb, G. Troster, M. Jones, T. Martin, Z. Nakad, Proc IEEE. 2003, 91(12), 1995-2018; Post, M. Orth, P. Russo, N. Gershenfeld, IBM Syst J. 2000, 39(3-4), 840-860]. Modulations of conductivity and optical transmission have been the two most common strategies to sense various physical stimuli such as pressure (or tactile forces) and humidity [M. Rothmaier, M. P. Luong, F. Clemens, Sensors. 2008, 8(7), 4318-4329; J. F. Gu, S. Gorgutsa, M. Skorobogatiy, Appl. Phys. Lett. 2010, 97(13), 133305]. To achieve the required flexibility and conformability, various methods have been proposed: for pressure measurements, multicore fibers consisting of layers of soft dielectric and conductive polymers or thin metal films were used to form capacitive structures [J. F. Gu, S. Gorgutsa, M. Skorobogatiy, Appl. Phys. Lett. 2010, 97(13), 133305]. The applied pressure changes the thickness of the soft dielectric sandwiched between two conductive concentric layers where the altered capacitance can be sensed as an indicator of applied pressure. These structures were either used by itself or with a second orthogonal fiber where the capacitance formed at the intersection point was sensed [Mattmann, F. Clemens, G. Troester, Sensors. 2008, 8(6), 3719-3732; Y. Hasegawa, M. Shikida, D. Ogura, Y. Suzuki, K. Sato, J Micromech Microengineering. 2008, 18(8), 085014; H. Lee, S. Chang, E. Yoon, J Microelectromech Syst. 2006, 15(6), 1681-1686]. In either case, these capacitive fibers were integrated into the woven textile through embroidering. Most of these studies used standard cleanroom deposition techniques (e.g., sputtering, evaporation, etc.) and complex patterning methods to coat fibers with conductive and dielectric layer [Mattmann, F. Clemens, G. Troester, Sensors. 2008, 8(6), 3719-3732; H. Lee, S. Chang, E. Yoon, J Microelectromech Syst. 2006, 15(6), 1681-1686; K. Cherenack, C. Zysset, T. Kinkeldei, N. Muenzenrieder, G. Troester, Adv Mater. 2010, 22(45), 5178-5182]. In another similar technique, conventional microfabrication processes have been used to build fabric-like capacitive structures with soft dielectric substrates overlaid with a matrix of conductive threads on both sides [M. Sergio, N. Manaresi, F. Campi, R. Canegallo, M. Tartagni, R. Guerrieri, IEEE J Solid State Circuits. 2003, 38(6), 966-975]. These microdevices were, then, cut into ribbons and woven into fabrics. A third method has been embroidering optical fibers into textiles which demonstrated modulated transmission properties with applied pressure [K. Cherenack, C. Zysset, T. Kinkeldei, N. Muenzenrieder, G. Troester, Adv Mater. 2010, 22(45), 5178-5182; Grillet, D. Kinet, J. Witt, M. Schukar, K. Krebber, F. Pirotte, A. Depre, IEEE Sensors Journal. 2008, 8(7-8), 1215-1222].

Conductive electrodes were also fabricated onto woven fabrics through sewing or embroidering to sense by conducting body potentials to external circuits. These conductive electrodes were mostly made of silver-coated nylon conductive threads [L. Beckmann, C. Neuhaus, G. Medrano, N. Jungbecker, M. Walter, T. Gries, S. Leonhardt, Physiol. Meas. 2010, 31(2), 233-247; T. Kannaian, R. Neelaveni, G. Thilagavathi, Journal of Industrial Textiles. 2013, 42(3), 303-318]. Knitted fabrics made of silver-coated polyamide, or cotton yarn wrapped with stainless steel fibers were also used to form such electrodes [L. Beckmann, C. Neuhaus, G. Medrano, N. Jungbecker, M. Walter, T. Gries, S. Leonhardt, Physiol. Meas. 2010, 31(2), 233-247]. Nylon knitted fabrics also were coated with silver to manufacture biopotential electrode patches [L. Beckmann, C. Neuhaus, G. Medrano, N. Jungbecker, M. Walter, T. Gries, S. Leonhardt, Physiol. Meas. 2010, 31(2), 233-247]. In another study, conductive yarns including silver-coated fibers and nonconductive synthetic yarns were woven together to form a fabric band [T. Finni, M. Hu, P. Kettunen, T. Vilavuo, S. Cheng, Physiol. Meas. 2007, 28(11), 1405-1419; L. Rattfaelt, M. Linden, P. Hult, L. Berglin, P. Ask, Med. Biol. Eng. Comput. 2007, 45(12), 1251-1257]. To sense wetness, copper wires were woven as warp and weft and electrical connection at the cross-over points were detected [Francesco, D. Costanzo, P. Salvo, D. Rossi, "Towards the Measurement of Sweat Rate via Wearable Sensors", in Proceedings of Personalised Health, May 2007, Greece; Pereira, T., Silva, P., Carvalho, H., & Carvalho, M. "Textile moisture sensor matrix for monitoring of disabled and bed-rest patients". In IEEE EUROCON-International Conference on Computer as a Tool (EUROCON), Apr. 2011, 1-4].

In all of the methods described above, the yarns employed were either all capacitive (for pressure sensing) or all conductive (for biopotential and wetness sensing) and were fabricated using expensive and complex cleanroom techniques. The sensing strategies examined thus far were applied to several applications. Flexible touch sensors were obtained through the capacitive pressure sensing mechanisms for haptic and rehabilitation applications [H. Lee, S. Chang, E. Yoon, J Microelectromech Syst. 2006, 15(6), 1681-1686; J. F. Gu, S. Gorgutsa, M. Skorobogatiy, arXiv preprint arXiv:1106.3881. 2011; S. Gorgutsa, J. F. Gu, M. Skorobogatiy; Smart Materials & Structures. 2012, 21(1), 015010; Parkova, A. Vališevskis, A. Kašurins, A. Vilumsone, "Integration of Flexible Keypad into Clothing," presented at Proceedings of the 8th International Scientific and Practical Conference "Environment. Technology. Resources."—Rezekne 2011, 173-181]. Electroconductive textile-based electrodes were embedded to chest-bands and bed sheets for electrocardiogram (ECG) measurements and respiratory rate detection for cardio-pulmonary monitoring [L. Beckmann, C. Neuhaus, G. Medrano, N. Jungbecker, M. Walter, T. Gries, S. Leonhardt, Physiol. Meas. 2010, 31(2), 233-24; L. Grajales, I. V. Nicolaescu, Wearable multisensor heart rate monitor, Proc. 3th Int. Workshop on Wearable and Implantable Body Sensor Networks, Boston, 2006, 157-61; S. Kim, S. Leonhardt, N. Zimmermann, P. Kranen, D. Kensche, E. Muller, C. Quix, "Influence of contact pressure and moisture on the signal quality of a newly developed textile ECG sensor shirt," presented at Medical Devices and Biosensors, 2008. ISSS-MDBS 2008. 5th International Summer School and Symposium on 2008; M. Peltokangas, J. Verho, A. Vehkaoja, IEEE Transactions on Information Technology in Biomedicine. 2012, 16(5), 935-942]. These ECG electrodes were analyzed extensively and found to demonstrate similar performance with standard Ag/AgCl electrodes [L. Beckmann, C. Neuhaus, G. Medrano, N. Jungbecker, M. Walter, T. Gries, S. Leonhardt, Physiol. Meas. 2010, 31(2), 233-247; S. Park, Y. Noh, S. Park, H. Yoon, Med. Biol. Eng. Comput. 2008, 46(2), 147-158; J. Coosemans, B. Hermans, R. Puers, Sensors and Actuators A-Physical. 2006, 130, 48-53; M. Ishijima, Med. Biol. Eng. Comput. 1997, 35(6), 685-690; J. C. Marquez, F. Seoane, E. Valimaki, K. Lindecrantz, Conference proceedings: Annual International Conference of the IEEE Engineering in Medicine and Biology Society, IEEE Engineering in Medicine and Biology Society. Conference. 2009, 2009, 4816-9; P. Scilingo, A. Gemignani, R. Paradiso, N. Taccini, B. Ghelarducci, D. De Rossi, IEEE Transactions on Information Technology in Biomedicine. 2005, 9(3), 345-352; L. Rattfaelt, M. Linden, P. Hult, L. Berglin, P. Ask, Med. Biol. Eng. Comput. 2007, 45(12), 1251-1257; J. Riistama, J. Lekkala, Conference proceedings: . . . Annual International Conference of the IEEE Engineering in Medicine and Biology Society. IEEE Engineering in Medicine and Biology Society. Conference. 2006, 1, 6021-4; Searle, L. Kirkup, Physiol. Meas. 2000, 21(2), 271-283; M. A. Mestrovic, R. J. N. Helmer, L. Kyratzis, D. Kumar, Preliminary study of dry knitted fabric electrodes for physiological monitoring 2007]. Such conductive textile based armbands were used to detect the movement of arms through electromyograms (EMG) for prosthetic applications [T. Finni, M. Hu, P. Kettunen, T. Vilavuo, S. Cheng, Physiol. Meas. 2007, 28(11), 1405-1419; Tao, H. Zhang, Z. Wu, G. Li, "Real-time performance of textile electrodes in electromyogram pattern-recognition based prosthesis control", presented at Biomedical and Health Informatics (BHI), 2012 IEEE-EMBS International Conference; Li, Y. Geng, D. Tao, P. Zhou, Performance of Electromyography Recorded Using Textile Electrodes in Classifying Arm Movements, 2011; T. Linz, L. Gourmelon, G. Langereis, "Contactless EMG sensors embroidered onto textile," presented at 4th International Workshop on Wearable and Implantable Body Sensor Networks, 2007]. These were also used to detect electroencephalography (EEG) waves [J. Lofhede, F. Seoane, M. Thordstein, "Soft textile electrodes for EEG monitoring," presented at Information Technology and Applications in Biomedicine (ITAB), 2010 10th IEEE International Conference; J. Lofhede, F. Seoane, M. Thordstein, Sensors. 2012, 12(12), 16907-16919].

SUMMARY OF THE INVENTION

Sensing environmental cues has been important for almost all electrical systems. One of the widely used sensors in consumer electronics is a tactile sensor, commonly utilized in touchpads and touchscreens in smartphones and tablet personal computers (PCs). These sensors are mostly rigid, limiting their application in industries that mandate flexible sensors. With advances in microfabrication technology, the development of small sized flexible sensors has been facilitated where flexible tactile sensors were widely studied [A. Charalambides and S. Bergbreiter, "All-elastomer in-plane MEMS capacitive tactile sensor for normal force detection," in 2013 IEEE, 2013, no. 1, pp. 1-4; E. Hwang, J. Seo, and Y. Kim, "A Polymer-based Flexible Tactile Sensor for Normal and Shear Load Detection," in IEEE MEMS, 2006, no. January, pp. 714-717; H. Lee, S. Chang, and E. Yoon, "A Capacitive Proximity Sensor in Dual Implementation with Tactile Imaging Capability on a Single Flexible Platform for Robot Assistant Applications," in 19th IEEE International Conference on MEMS, 2006, no. January, pp. 606-609; Y. Hasegawa, M. Shikida, D. Ogura, Y. Suzuki, and K. Sato, "Fabrication of a wearable fabric tactile sensor produced by artificial hollow fiber," J. Micromechanics Microengineering, vol. 18, no. 085014, August 2008; M. Sergio, N. Manaresi, M. Tartagni, R. Guerrieri, and R. Canegallo, "A Textile Based Capacitive Pressure Sensor," in Proceedings of IEEE Sensors, 2002, pp. 1625-1630]. Most of these sensors were fabricated using silicon-based microfabrication technology [A. Charalambides and S. Bergbreiter, "All-elastomer in-plane MEMS capacitive tactile sensor for normal force detection," in 2013 IEEE, 2013, no. 1, pp. 1-4; E. Hwang, J. Seo, and Y. Kim, "A Polymer-based Flexible Tactile Sensor for Normal and Shear Load Detection," in IEEE MEMS, 2006, no. January, pp. 714-717; H. Lee, S. Chang, and E. Yoon, "A Capacitive Proximity Sensor in Dual Implementation with Tactile Imaging Capability on a Single Flexible Platform for Robot Assistant Applications," in 19th IEEE International Conference on MEMS, 2006, no. January, pp. 606-609], while some were fabricated using a textile approach [Y. Hasegawa, M. Shikida, D. Ogura, Y. Suzuki, and K. Sato, "Fabrication of a wearable fabric tactile sensor produced by artificial hollow fiber," J. Micromechanics Microengineering, vol. 18, no. 085014, August 2008; M. Sergio, N. Manaresi, M. Tartagni, R. Guerrieri, and R. Canegallo, "A Textile Based Capacitive Pressure Sensor," in Proceedings of IEEE Sensors, 2002, pp. 1625-1630]. Although other sensing principles like strain gauge can be employed [E. Hwang, J. Seo, and Y. Kim, "A Polymer-based Flexible Tactile Sensor for Normal and Shear Load Detection," in IEEE MEMS, 2006, no. January, pp. 714-717], capacitive sensing methodology dominates tactile detection for its ease of characterization and implementation [H. Lee, S. Chang, and E. Yoon, "A Capacitive Proximity Sensor in Dual Implementation with Tactile Imaging Capability on a Single Flexible Platform for Robot Assistant Applications," in 19th IEEE International Conference on MEMS, 2006, no. January, pp. 606-609; Y. Hasegawa, M. Shikida, D. Ogura, Y. Suzuki, and K. Sato, "Fabrication of a wearable fabric tactile sensor produced by artificial hollow fiber," J. Micromechanics Microengineering, vol. 18, no. 085014, August 2008; M. Sergio, N. Manaresi, M. Tartagni, R. Guerrieri, and R. Canegallo, "A Textile Based Capacitive Pressure Sensor," in Proceedings of IEEE Sensors, 2002, pp. 1625-1630]. Many of these flexible tactile sensors are designed for either robotic applications or human interface to monitor force distribution.

Wearable biopotential detection devices require a comfortable well-being monitor that can easily be used at-home without having to be in a lab environment. This is especially true for ECG recording. For ubiquitous deployment, the electrodes for biopotential detection should be flexible, low-cost, and free of conductive gel or paste that is the hallmark of wet electrodes. Flexible printed circuit and MEMS technology enabled recordings without gels [H. L. Kim, Y. H. Kim, and Y. J. Kim, "Miniature electrocardiography sensor using a flexible printed circuit and MEMS technology," in Proceedings of IEEE International Conference on Multisensor Fusion and Integration for Intelligent Systems, 2008, no. 1, pp. 545-550]. Although less efficient due to having a higher impedance at the electrode-tissue interface, such dry electrodes are still advantageous in wearable biopotential detection devices for their simplicity and comfort.

Fluid detection has been commonly used in multiple industries for various specific applications. In the automotive industry, fluid sensing devices have been fabricated using MEMS technologies for detecting fuel leaks and moisture [K. Meredith, M. Safai, and G. Georgeson, "New MEMS Technologies for Integrated Vehicle Health Management and Fluid Sensing Applications," in 2009 IEEE Aerospace conference Proceedings, 2009]. In the biomedical industry, wetness detection is particularly important for measuring dehydration levels [J. M. Fouke, A. D. Wolin, M. R. Neuman, and E. R. Mcfadden, "Sensor for Measuring Surface Fluid Conductivity In Vivo," IEEE Trans. Biomed. Eng., vol. 35, no. 8822622, pp. 877-881, 1988] and detection of bleeding.

The currently available sensing devices can perform only one of the aforementioned sensing schemes. However, several biomedical applications require concurrent measurement of movement of the subject, recording of the biopotentials and detection of wetness caused by bodily fluids such as blood, urine or sweat. In view of the foregoing, there is a desire to provide improved biomedical sensors and techniques.

Embodiments of the invention include a strategically designed textile structure, assembled from co-extruded multicomponent fibers (CoMFi), to produce FIRST that are capable of generating useful electrical responses under various stimuli. The unique structural and material characteristics of CoMFi are utilized to create sensing textile elements or "texels" for concurrent detection of multiple physical parameters.

The success of electronic textile (e-textile) efforts requires the ability to (i) integrate various electronic functionalities into textiles in a truly unobtrusive manner, and (ii) preserve the unique and essential "textile" characteristics (strength, flexibility, texture, softness, porosity, comfort, and stability (environmental and in-use)) of fibrous structures. The unique properties of textiles (e.g. flexibility) arise from both the inherent fiber material properties as well as the hierarchical architecture of the fiber assembly.

Embodiments of the smart textile patches of the present invention provide an effective and inconspicuous way to introduce desired electrical characteristics at the fiber level by benefitting from its hierarchical architecture.

Embodiments of the present invention relate to smart fabric patches integrated into clothing or other textiles where the fibers of the fabric patch form distributed sensory elements (texels) and can simultaneously measure tactile forces, moisture/wetness, and biopotentials. The fibers are extruded from polymers and woven into fabrics using traditional textile manufacturing processes enabling very low production costs so that the patches can be incorporated into many different items throughout many industries.

The invention is unique in that it is scalable and can be applied to (i) functionalize textile fibers through precise cross-sectional architecture using a commercially available process (e.g., bicomponent extrusion) for integrating sensing into wearables, (ii) interlace these fibers into sensory fabric substrates using established processing technology (e.g., weaving) capable of high-speed, low-cost, and large-area roll-to-roll production, and (iii) connect state-of-the-art silicon based rigid electronics to this fabric to integrate smart sensing algorithms and wireless data transfer for various practical applications.

The fiber-based sensory textiles are fundamentally translational and transformative as these potentially obviate the limitations imposed by substrate size for processing in conventional semiconductor-based sensors and open up a very attractive possibility of roll-to-roll processing of flexible sensor systems. Therefore, the sensory properties of textile structure at multiple scales complements the research efforts by others to pave the way towards building fully textile flexible electronic sensor systems.

The smart textile patches can be implemented in many different applications in different industries. Some examples are described below.

Biomedical Applications

Medical/Therapeutic Products: The patches can be incorporated into compression garments such as stockings/sleeves/gloves in the treatment of varicose venous diseases (ulcers, thrombosis, etc.), as well as bandages for wound care and scar management for burn victims. The patches can also be incorporated into disposable products, such as diapers for infants and bedridden elderly to monitor their movement, heart rate, respiratory rate, and urination.

The patches can be incorporated into fabrics or applied to skin with an adhesive. The patches can also be incorporated into braces or casts, worn in belts or headbands/wristbands, implemented in shoes (as in insert or integrally applied to shoe padding). The patches can also be used in monitoring the health of animals (pets, zoos, endangered animals, etc.).

Exercise: The patches can be incorporated into textile-based chest-straps to monitor exercise physiology where the simultaneous detection of movement can be used to obtain adaptive filtering of the motion artifacts from the physiological signals.

Military/Law Enforcement Applications

The patches can be incorporated to detect the impact or penetration of bullets (or other projectiles) during a military combat scenario where the forces acting on the smart fabric incorporated into the combatant's clothing could be used to detect not only the impact, but also whether it penetrates into the clothing and causes any bleeding. Detection of the vital signs would provide the status of the combatant's health status after the impact and provide information for remote triage, diagnosis and decision-making.

The patches can be used for non-medical defense applications such as sensing on fabrics (tents/tarps/walls/seats, etc.), monitoring pressure and temperature with conformal fabric sensors, clandestine monitoring with small disposable patches on remote objects, monitoring vehicle traffic on roads, integrated into uniforms or ruck sacks for environmental monitoring (in addition to health of user).

The patches can be integrated into prisoner uniforms, restraints, and fabrics in a holding/prison cell for monitoring the prisoner.

Security and Surveillance Applications

The patches can be incorporated, for example, in carpets to monitor unauthorized entry into restricted space or to simply count the number of people present at an event.

The patches can be utilized for remote sensing and clandestine monitoring. The patches can be applied, woven into or implanted in packages to monitor for security purposes or to provide tamper-resistant mail or packages.

Communication/Entertainment Applications

The patches arranged appropriately in clothing or other textile substrates can work as input devices for communication systems (soft keyboard or touchpad). These can also be part of the sensory system necessary for haptic input/output devices.

Sports Applications

The patches can be incorporated in athletic wear (socks, graduated compression stockings, undergarments, etc.) for fitness tracking, quantified self, coaches monitoring players, or self-training health monitoring. For example, the patches can be incorporated in athletic wear to monitor the level of compression on muscles and help improve muscle performance by improving skeletal muscle pump, increase venous velocity, and alleviate delayed onset of muscle soreness.

Transportation Applications

The patches can be integrated with roadways and traffic sensors to monitor traffic.

Consumer Applications

The patches can be incorporated into bedding materials such as sheets, blankets and pillows, and furniture, such as hardgoods and softgoods, carpets, and curtains/drapes.

Several biomedical applications utilize concurrent measurement of movement of the subject, sensing of the biopotentials and detection of wetness caused by bodily fluids. The patch may use flexible capacitive tactile sensing arrays for concurrent monitoring of biopotential and moisture (or wetness). This may be enabled by designing the cross-section of the extruded fibers in a specific "H" shape where the intersection of fibers creates a capacitive sensor and the change in the gap is used for estimating the presence and the value of tactile forces. The capacitive plates may act as biopotential sensors when coupled to the skin and the presence of conductive fluids in-between the plates can be sensed through impedance spectroscopy. A microfabricated version of the patch and miniaturized circuit front-end using commercial-of-the-shelf components is provided to interface the sensors and wirelessly transmit the data through a Bluetooth low energy link. Using the designed circuitry, the force applied to the texel in the array has been estimated through capacitive sensing with a linear change in the capacitance with the applied force. The same sensor was used to detect ECG waveforms and sense the presence of wetness and salinity using impedance characterization.

It is noted that the electrode structures and impedance sensors disclosed herein can be used to track and measure hydration. Further, the electrode structures and impedance sensors disclosed herein can be used to analyze urine/sweat liquid (or moisture) content with the analysis of impedances obtained with the on-board potentiostat by applying electrochemisty methods such as, but not limited to, amperometry, cyclic voltammetry, electrochemical impedance spectroscopy, voltage excursion analysis, dielectric spectroscopy, and the like.

As used herein, the term "multi-component strand" refers to a flexible component with a cross-sectional arrangement of two or more materials.

As used herein, the term "texel" means an intersection (or cross-over area or point) of a row (filling) and a column (warp) of a substrate (e.g., woven fabric, interlaced paper strips, etc.).

In one embodiment, the invention provides a sensing system comprising a first set of strands, a second set of strands, and a circuit. The first set of strands include a plurality of first multi-component strands, each of the first multi-component strands including a conductive portion and a non-conductive portion. The second set of strands includes a plurality of second multi-component strands, each of the second multi-component strands including a conductive portion and a non-conductive portion, and a plurality of third multi-component strands, each of the third multi-component strands including a conductive portion and a non-conductive portion, the third multi-component strands being different than the first multi-component strands and the second multi-component strands. The second multi-component strands are oriented orthogonal relative to the first multi-component strands to form a plurality of first texels, and the third multi-component strands are oriented orthogonal relative to the first multi-component strands to form a plurality of second texels. The circuit is electrically coupled to the first texels to detect a change in capacitance or a change in impedance at the first texels, the circuit electrically coupled to the second texels to detect a signal at the second texels.

In another embodiment, the invention provides a sensor patch comprising a first sensor formed at an intersection of a first multi-component strand and a second multi-component strand, a second sensor formed at an intersection of a third multi-component strand and the first multi-component strand, and a circuit electrically coupled to the first sensor to detect a change in capacitance and a change in impedance, the circuit electrically coupled to the second sensor to detect a biopotential from a user.

In a further embodiment, the invention provides a sensor patch comprising a plurality of first multi-component strands, a plurality of second multi-component strands, a plurality of third multi-component strands, a first texel formed at a first intersection of one of the first multi-component strands and one of the second multi-component strands, and a second texel formed at a second intersection of one of the first multi-component strands and one of the second multi-component strands, and a third texel formed at a third intersection of one of the first multi-component strands and one of the third multi-component strands. The first texel is configured to detect presence of fluid, the second texel is configured to detect an applied force, and the third texel is configured to detect a biopotential.

In yet another embodiment, the invention provides a flexible array of sensors comprising a first layer including a plurality of first multi-component strands interlaced with a plurality of second multi-component strands, a second layer including a plurality of third multi-component strands interlaced with the first multi-component strands, a plurality of first sensors formed in the first layer, the first sensors configured to detect a change in capacitance, a plurality of second sensors formed in the first layer, the second sensors configured to detect a change in impedance, and a plurality of third sensors formed in the second layer, the third sensors configured to detect a signal.

In yet a further embodiment, the invention provides a method of manufacturing an array of sensors. The method comprises extruding a plurality of first multi-component strands, extruding a plurality of second multi-component strands, weaving or braiding a first group of the plurality of first multi-component strands into a structure, weaving or braiding a second group of the plurality of first multi-component strands into the structure orthogonal to the first group of the plurality of first multi-component strands to form a plurality of first texels, and weaving or braiding the plurality of second multi-component strands into the structure orthogonal to the first group of the plurality of first multi-component strands to form a plurality of second texels.

In another embodiment, the invention provides a method of manufacturing a sensor. The method comprises providing a substrate, depositing a first metal on the substrate, depositing first and second portions of a non-conductive material on the first metal, the first and second portions of the non-conductive material defining a space therebetween, electroplating to form a second metal in the space, depositing a third metal on the second metal and the first and second portions of the nonconductive material, depositing third and fourth portion of a non-conductive material on the first and second portions, respectively, and on portions of the third metal, and removing the substrate, the first metal, and the second metal to form the sensor.

Embodiments of the present invention may be implemented as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Other aspects of the invention will become apparent by consideration of the detailed description and accompanying drawings.

BRIEF DESCRIPTION OF THE DRAWINGS

FIG. 4 illustrates formation of texels optimized for biopotential, tactile or wetness sensing (A); relevant texels can be distributed vertically (B) or horizontally (C); the sensors are distributed throughout the textile fabric (D).

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Embodiments of the invention provide low cost multi-component fiber extrusion techniques to obtain a particular cross-sectional geometry of the CoMFi for concurrent detection of pressure, moisture, and biopotentials. The unique cross-sectional patterning of the fiber allows for capacitive fibers with exposed resistive parts for a hybrid operation. This provides for the combination of all the above sensing efforts to a single fabric structure using compatible materials.

Embodiments of the invention use a woven network of fibers with conducting and insulating cross-sectional segments to implement electronic sensing capabilities. One of the key features utilizes the precise structure and conductive properties of orthogonally interlaced multi-component strand in a woven fabric (from single texel to an array of texels) to sense mechanical forces, record biopotentials, and measure impedances.

Working Principle of Fiber IntegRated Sensor Technologies (FIRST)

Figure 2:
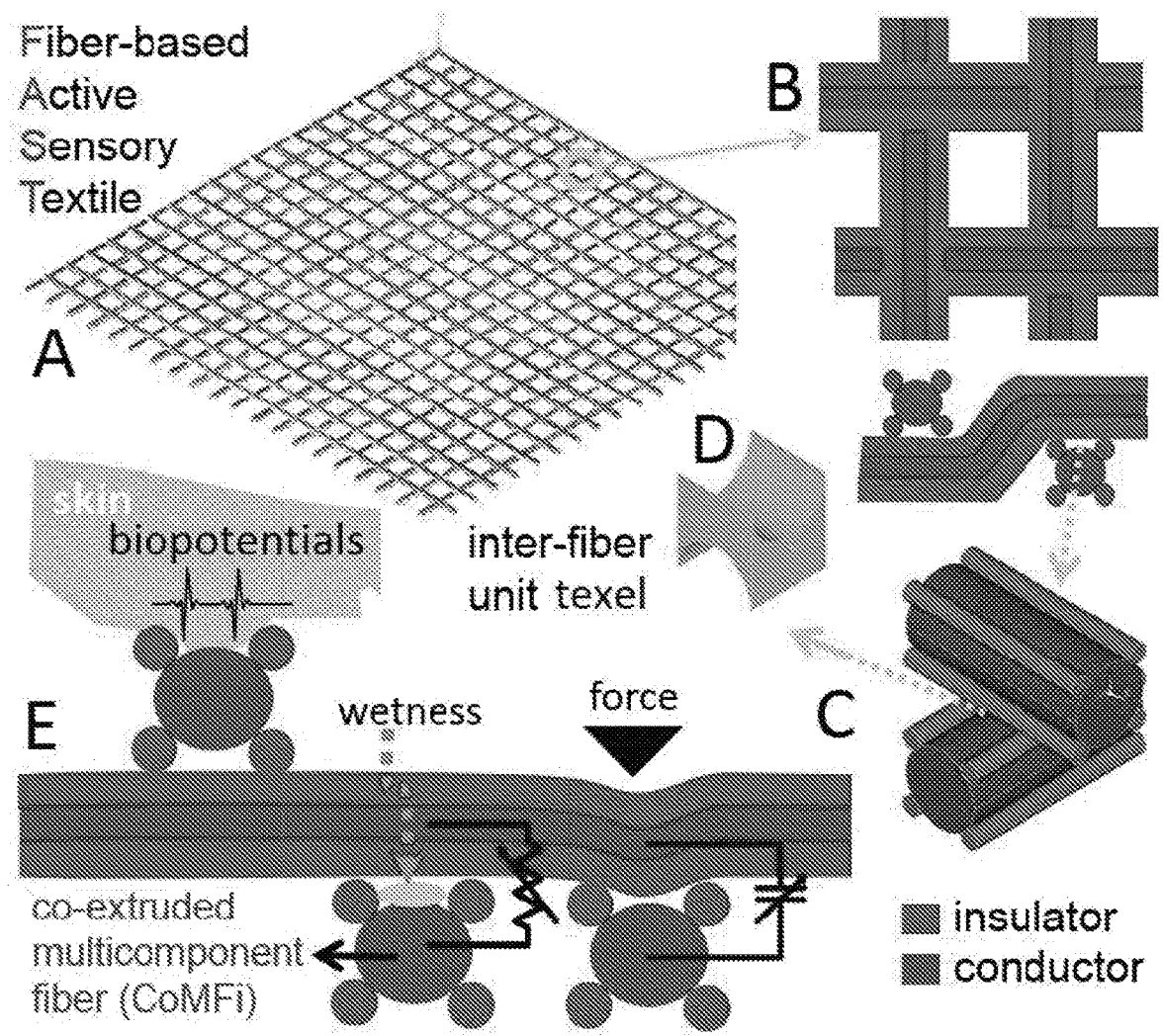
FIG. 2 is a pictorial representation of a sensing array (A, B) and its operation principle (E). The texel between the CoMFi intersections in a larger array shown on an ANSYS plot (A,C,D).
Figure 3:
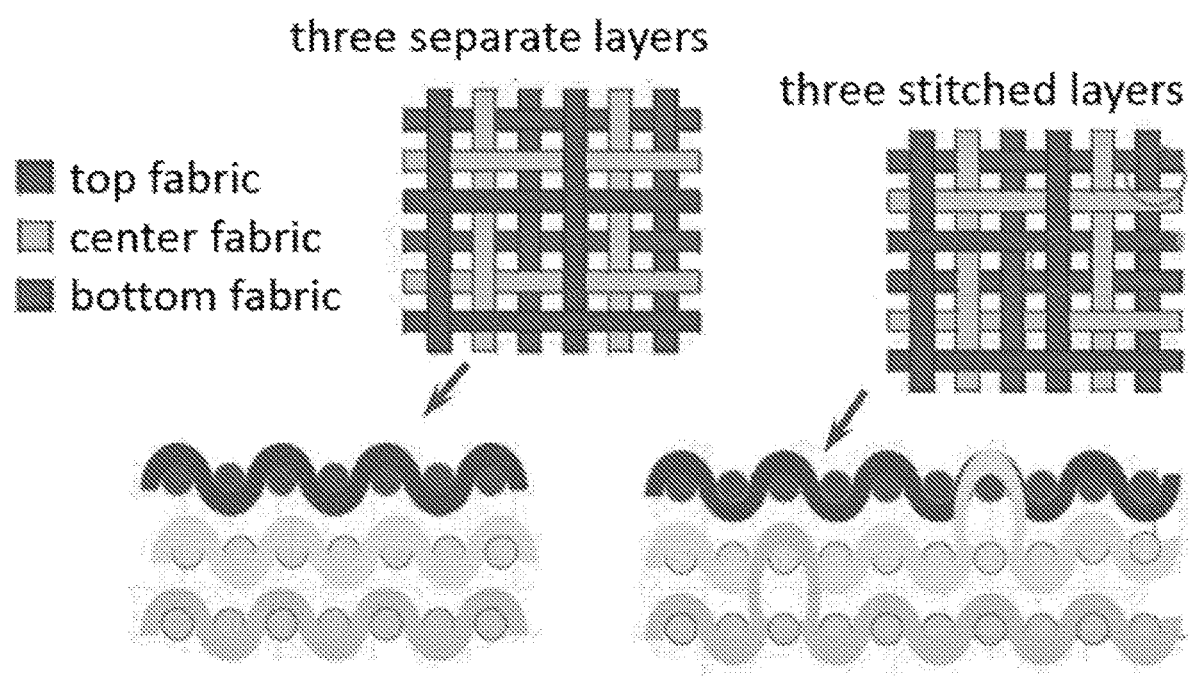
FIG. 3 is a pictorial representation of a three-dimensional array of texels where fibers are woven into a fabric with multiple "stitched" layers, in which some of the fibers traverse from one layer to another.

As illustrated in FIG. 2, embodiments of the invention utilize the unique orthogonal structure of FIRST where the intersection (cross-over) of each row (filling) and column (warp) of yarns, defined as a sensor "texel," is used to sense three different physiologically relevant parameters. The impedance of the texel is used to detect applied tactile forces as well as presence of moisture and wetness. The intermediate conducting layer of the multi-component strand is used as surface electrodes to record biopotentials. The multi-component strands are weaved in a multiple layer structure to form a fabric where the fabric eventually has a 3-dimensional array of texels as illustrated in FIGS. 3 and 4 to achieve distributed sensing. One of the primary considerations in the design of multi-component strands is the component cross-sectional geometry as well as the electrical and mechanical behavior of the individual materials.

Designing the Multi-Component Strand Texel

With reference to FIG. 2, the multicomponent polymeric fiber, or multi-component strand, is a monofilament yarn made of a conductive layer at the center surrounded by a patterned insulating cladding polymer. Initially, three different cross-sections as illustrated in FIG. 4 are used to provide efficient electrodes and capacitive/impedance textile arrays. Over time, the multi-component strand texel is formed of a single cross-sectional area as illustrated in FIG. 2 for all three sensors. The overall dimension of the fiber and that of the various segments depends largely on the practical limits of the processes (e.g., extrusion, weaving) and behavior of the materials. In an initial design, the fiber diameter is in the range of 300-400 µm with the intermediate conducting layer thickness in the range of 50-100 µm. These are the typical maximum sizes likely to produce flexible and conformal fabric structures when woven. The final dimensions of the fiber and its cross-sectional segments are dependent upon a number of design constraints necessary for the functioning of the FIRST system. These constraints include the positioning of the insulating tips around the core so that undesired electrical contact between the conducting cladding layers of neighboring fibers in a fabric is eliminated. Other critical characteristics of CoMFi include the conductivity of the core conductor which should be in the range of $10^{-5}$-$10^{-8}$ S/cm. Based on the intended application, the FIRST may also require optimal local deformation to conform to the surface of the body, in which case stiffness of the fiber (in bending and compression) should also be moderately low to allow sufficient deformation for contact. Therefore, the choice of materials (polymer and conductive fillers) for CoMFi is primarily dictated by their potential electrical and mechanical properties as well as the ease of processing (i.e., extrusion).

Figure 5:
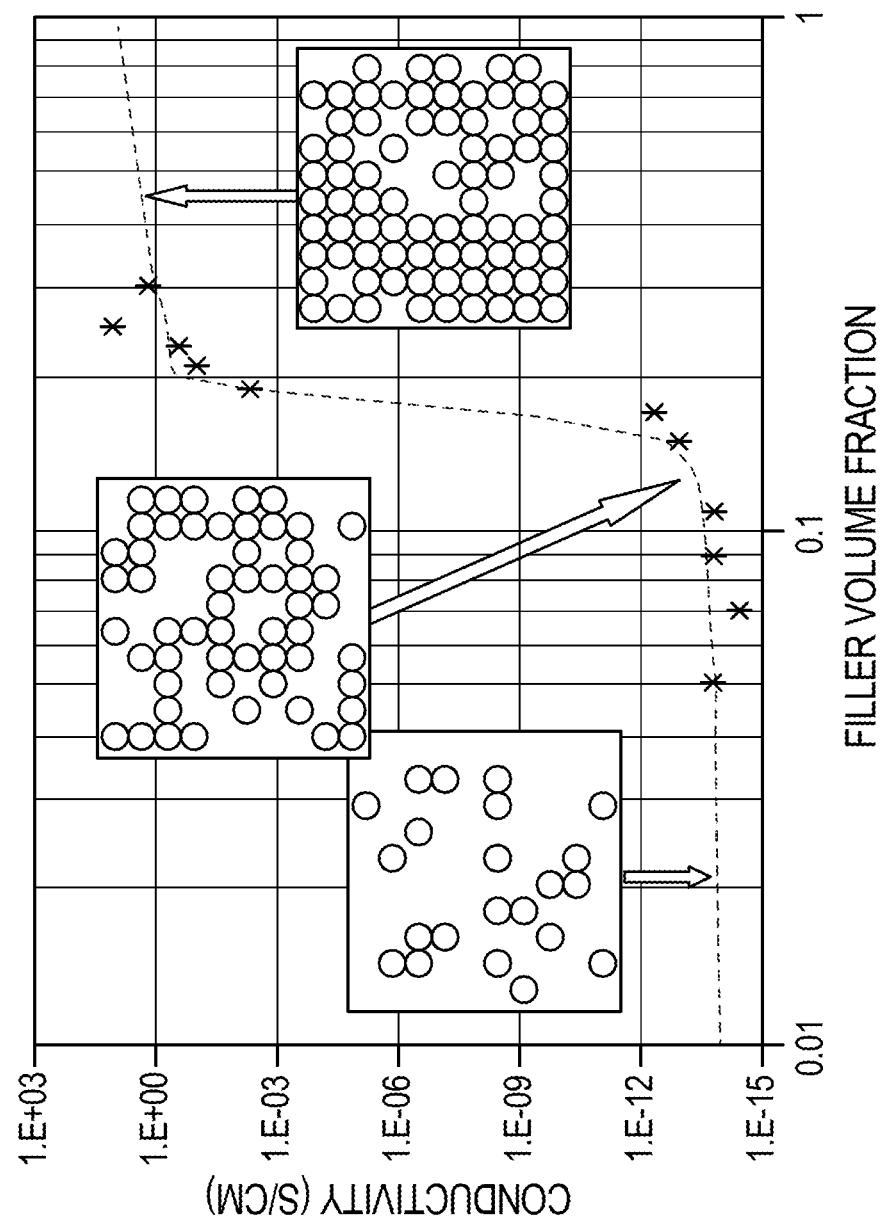
FIG. 5 is a graphical representation of the onset of percolation at Dc (blue) in a composite material.

Conductivity in the core layer of CoMFi is engendered by incorporating conductive particles into a base polymer. Therefore, understanding the percolation behavior of the particular polymer/particle nanocomposites is essential in formulating this segment. Percolation represents a standard model to describe the spatial distribution of species within disordered systems [Stauffer, D. & Aharony, A. Introduction to Percolation Theory, Taylor and Francis, London 1985; Sahimi, M. Flow and Transport in Porous Media and Fractured Rock 12, VCH, Weinheim, Germany, 1995]. It is defined as the development of long-range connectivity (networking) in a random system as illustrated in FIG. 5 [Youngs, Journal of Physics D-Applied Physics. 2002, 35(23), 3127-3137]. According to percolation theory, conduction of electricity through a composite can be described by introducing the parameter φ, the volume fraction of the conducting phase. The transition of the composite form insulating to conducting occurs abruptly as φ is increased and is often associated with the development of a continuous electrical pathway in the composite. The bulk conductivity σ of a percolating composite with volume concentration φ of the conducting phase behaves as a power law of the form [Stauffer, D. & Aharony, A. Introduction to Percolation Theory, Taylor and Francis, London 1985; McCall, N. Dimitrov, K. Sieradzki, J. Electrochem. Soc. 2001, 148(6), E290-E293; M. Sahimi, Heterogeneou+B118s Materials: Linear transport and optical properties, Vol. 22, Springer Verlag, 2003; L. Flandin, T. Prasse, R. Schueler, K. Schulte, W. Bauhofer, J. Cavaille, Physical Review B. 1999, 59(22), 14349-14355], $\sigma=\sigma_o (\varphi-\varphi_c)^t$ where $\sigma_o$ is a constant of proportionality, and $\varphi_c$ is the critical volume fraction of conductive filler at the percolation threshold. The exponent t is characteristic of the transition from dispersed filler particles to networked particles, and is assumed to be universal [R. Strumpler, J. Glatz-Reichenbach, Journal of Electroceramics. 1999, 3(4), 329-346; Clerc, V. Podolskiy, A. Sarychev, The European Physical Journal B-Condensed Matter and Complex Systems. 2000, 15(3), 507-516]. In many polymer composites containing conductive particles, the interparticle electrical contacts can be attributed to tunneling [P. Sheng, E. Sichel, J. Gittleman, Phys. Rev. Lett. 1978, 40(18), 1197-1200. 95], and the conduction network forms a well-defined percolation-like network [Balberg, Phys. Rev. Lett. 1987, 59(12), 1305-1308] referred to as tunneling-percolation system.

The percolation behavior of carbonaceous particles, such as carbon nanofibers (CNF), carbon black (CB), and carbon nanotubes (CNT) contained in polymer systems has been the subject of numerous studies [S. Rul, F. Lefevre-Schlick, E. Capria, C. Laurent, A. Peigney, Acta Materialia. 2004, 52(4), 1061-1067; Martin, J. Sandler, M. Shaffer, M. Schwarz, W. Bauhofer, K. Schulte, A. Windle, Composites Sci. Technol. 2004, 64(15), 2309-2316; Najafi, K. Shin, Colloids Surf. Physicochem. Eng. Aspects. 2005, 257, 333-337; Koerner, W. Liu, M. Alexander, P. Mirau, H. Dowty, R. A. Vaia, Polymer. 2005, 46(12), 4405-4420; Y. S. Song, J. R. Youn, Carbon. 2005, 43(7), 1378-1385; X. Jiang, Y. Bin, M. Matsuo, Polymer. 2005, 46(18), 7418-7424; Loos, A. Alexeev, N. Grossiord, C. Koning, O. Regev, Ultramicroscopy. 2005, 104(2), 160-167; Zhang, R. Fu, M. Zhang, X. Dong, P. Lan, J. Qiu, Sensors and Actuators B-Chemical. 2005, 109(2), 323-328; H. Al-Saleh, U. Sundararaj, Carbon. 2009, 47(1), 2-22; T. Jeevananda, N. H. Kim, J. H. Lee, S. Basavarajaiah, M. V. D. Urs, C. Ranganathaiah, Polym. Int. 2009, 58(7), 775-780; Y. Geng, M. Y. Liu, J. Li, X. M. Shi, J. K. Kim, Composites Part A-Applied Science and Manufacturing. 2008, 39(12), 1876-1883; Z. Spitalsky, D. Tasis, K. Papagelis, C. Galiotis, Progress in Polymer Science. 2010, 35(3), 357-401; O. Park, T. Jeevananda, N. H. Kim, S. Kim, J. H. Lee, Scr. Mater. 2009, 60(7), 551-554; T. Jeevananda, Siddaramaiah, T. S. Lee, J. H. Lee, O. M. Samir, R. Somashekar, J Appl Polym Sci. 2008, 109(1), 200-210; Hong, J. Lee, P. Kalappa, S. G. Advani, Composites Sci. Technol. 2007, 67(6), 1027-1034; Liu, F. Luo, H. Wu, Y. Liu, C. Zhang, J. Chen, Advanced Functional Materials. 2008, 18(10), 1518-1525; S. Pfeifer, S. -. Park, P. R. Bandaru, J. Appl. Phys. 2010, 108(2), 024305; Bryning, M. Islam, J. Kikkawa, A. Yodh, Adv Mater. 2005, 17(9), 1186-1191; J. Liang, Q. Yang, J. Appl. Phys. 2007, 102(8), 083508]. The reported percolation threshold (vol %) ranges between 0.5 and 20% for CNF [H. Al-Saleh, U. Sundararaj, Carbon. 2009, 47(1), 2-22], <1% for CNT [S. Pfeifer, S. -. Park, P. R. Bandaru, J. Appl. Phys. 2010, 108(2), 024305; Bryning, M. Islam, J. Kikkawa, A. Yodh, Adv Mater. 2005, 17(9), 1186-1191] and 8-27% for CB [J. Liang, Q. Yang, J. Appl. Phys. 2007, 102(8), 083508] in a variety of polymer-matrix composites. Among these, CNTs have proven to be very effective as conductive fillers [T. Jeevananda, N. H. Kim, J. H. Lee, S. Basavarajaiah, M. V. D. Urs, C. Ranganathaiah, Polym. Int. 2009, 58(7), 775-780; Y. Geng, M. Y. Liu, J. Li, X. M. Shi, J. K. Kim, Composites Part A-Applied Science and Manufacturing. 2008, 39(12), 1876-1883; Z. Spitalsky, D. Tasis, K. Papagelis, C. Galiotis, Progress in Polymer Science. 2010, 35(3), 357-401; O. Park, T. Jeevananda, N. H. Kim, S. Kim, J. H. Lee, Scr. Mater. 2009, 60(7), 551-554; T. Jeevananda, Siddaramaiah, T. S. Lee, J. H. Lee, O. M. Samir, R. Somashekar, J Appl Polym Sci. 2008, 109(1), 200-210; Hong, J. Lee, P. Kalappa, S. G. Advani, Composites Sci. Technol. 2007, 67(6), 1027-1034]. The only drawback of CNTs as a nanofiller is their higher production cost [Liu, F. Luo, H. Wu, Y. Liu, C. Zhang, J. Chen, Advanced Functional Materials. 2008, 18(10), 1518-1525]. Therefore, the mass production of CNT based functional composite materials is difficult. Important advantages of CNF include its commercial availability in different aspect ratios, diameters and purity and its ease of dispersion relative to CNTs [H. Al-Saleh, U. Sundararaj, Carbon. 2009, 47(1), 2-22].

Material Selection and Preparation

The viscosity of the polymer melt is one of the key parameters that determine fiber formation characteristic of a polymer in melt extrusion and, in particular, in multicomponent fiber formation. The melt-flow rate (MFR) is one of the often-used polymer characteristics for melt extrusion and it has been correlated to more fundamental flow characteristics such as the zero-shear viscosity, molecular weight average, and molecular weight distribution [Shenoy, S. Chattopadhyay, V. Nadkarni, Rheologica Acta. 1983, 22(1), 90-101; Dutta, Rheologica Acta. 1984, 23(5), 565-569; K. Seavey, Y. Liu, N. Khare, T. Bremner, C. Chen, Ind Eng Chem Res. 2003, 42(21), 5354-5362; D. C. Rohlfing, J. Janzen, What's Happening in the Melt-Flow Plastometer: The Role of Elongational Viscosity. In Technical papers of the Annual Technical Conference-Society of Plastics Engineers Incorporated 1997 vol. 1, pp. 1010-1014]. The MFR quantifies the mass of polymer that is extruded by an extrusion plastometer over a fixed time (specified as the mass in grams that would be extruded in 10 minutes) under prescribed temperature and mechanical loading conditions. During the initial phase, MFR of the base polymer and the conducting particle loaded polymer composite is optimized. Another key performance characteristic of the CoMFi for FIRST is the ability of the fiber to deform (in bending and tensile modes) and recover. Therefore, relatively low Young's modulus and elastic recovery of the fiber is utilized during fiber formation.

In order to have compatibility in processing as well as interfacial adhesion between the conducting and insulating segments during use, the same base polymer throughout the cross-section of the CoMFi is used. The conductive segments of the fiber can be fabricated by incorporating carbonaceous (e.g. CB) or metallic (e.g. Ag) particles into a base polymer in appropriate amounts (above percolation threshold). A conductive polymer masterbatch is prepared (or acquired) by compounding the particles with the fiber forming polymer. The MFR of the masterbatch is very important because it indicates the relative ease with which a masterbatch can be distributed during a compounding operation or melt extrusion. Additives like CB have a pronounced effect on the viscosity of the polymer melt [J. L. White, J. W. Crowder, J Appl Polym Sci. 2003, 18(4), 1013-1038]. Therefore, a relatively high flow base polymer should be used as carrier, so that the resultant masterbatch possesses MFR conducive to extrusion.

Some of the candidate fiber forming polymers, including their MFR and Young's modulus values, are presented in Table 1.

TABLE 1

| Polymer | Young's modulus (MPa) | MFR (g/10 min) |
|---|---|---|
| Polypropylene (Various Moplen types by LyondellBasell) | 340-1500 | 3.5-25 |
| Polyamide (Various Ultramid types, by BASF) | 2000-5000 | 7.2-36 |
| Thermoplastic Elastomers (Various Elastollan types 1100 by BASF) | 10-1000 | 21-60 |

The polypropylene, and polyamide resins are available in a wide variety of MFRs and therefore can be potentially used to fabricate CoMFi with some variation in key properties. Thermoplastic elastomers (TPE) offer another viable choice. TPEs are block copolymers that combine stiff and flexible segments in the same polymer chain to produce the elastomeric behavior of high extensibility and high elastic recovery [R. Spontak, N. Patel, Current Opinion in Colloid & Interface Science. 2000, 5(5-6), 334-341]. TPEs are commercially available in many forms with a wide choice of processing conditions. Initially, thermoplastic polyurethanes (e.g Elastollan by BASF) are used as the base polymer, primarily because of their mechanical properties as well as availability in a wide-ranging melt flow characteristics.

CNF also is used as the conductive particle for the conductive layer of CoMFi. The choice of CNF as opposed to spherical particles derives from the fact that particles with high aspect ratio reach their percolation threshold at relatively low concentration. This is an important consideration because of the potential deterioration in flexibility of the nanocomposite at high particle loading levels. Typical vapor-grown CNF diameters range from 3 to 200 nm, but their length can vary from 0.1 to 10 µm [Nakano, K. Shimizu, S. Takahashi, A. Kono, T. Ougizawa, H. Horibe, Polymer. 2012, 53(26), 6112-6117]. In the same vein as their CNT analogs, CNFs possess attractive properties such as ultrahigh strength, high electrical conductivity, high corrosion resistance, and invariable mechanical properties over a wide temperature range (from cryogenic temperatures up to 1000° C.) [K. De Jong, J. Geus, Catalysis Reviews-Science and Engineering. 2000, 42(4), 481-510]. Due to inherently better dispersability and wettability, CNFs possess higher nucleation efficiency than single-wall CNTs [Shen, C. Zeng, L. J. Lee, Polymer. 2005, 46(14), 5218-5224]. Important advantages of CNF include its commercial availability in different aspect ratios, diameters and purity and its ease of dispersion relative to CNTs. Since the Young's modulus of CNF is lower than that of CNT, the increase in modulus achieved by incorporating CNFs into a polymer matrix is less pronounced than that obtained with CNTs, which is desirable here to produce highly conformable deformation sensors. The only potential drawback of CNF as a nanofiller in this context is its dimensions. If the thickness of the conducting polymer could not accommodate particles of this length, CB can be used instead where CB particles in a wide range of particle diameters (10-500 nm [A. Moskalyuk, A. N. Aleshin, E. S. Tsobkallo, A. V. Krestinin, V. E. Yudin, Physics of the Solid State. 2012, 54(10), 2122-2127]) and surface area (4.87-981.6 m2/g [Z. Li, J. Zhang, S. Chen, J. Electrostatics. 2009, 67(1), 73-75]) are commercially available. The actual cross-sectional shape of the melt extruded CoMFi depends critically on the melt viscosity of the component polymers and their thermal behavior. The initial cross-sectional shape is obtained after a few trials to adjust melt flow rate through polymer blending and control of melt temperature. Another important consideration is the cooling (or quenching) of the polymer melt subsequent to exit from the die. In general, the morphology (crystallization and molecular orientation) of a CoMFi depends strongly on its temperature history during extrusion and cooling [Ziabicki, Fundamentals of fibre formation: the science of fibre spinning and drawing, Wiley, London; New York 1976]. The rate of cooling can be controlled in a process over a wide range, from quenching by cold water to slower cooling in ambient air. The surface of a thick monofilament is likely to cool quickly upon quenching compared to the interior which cools slowly because of the very slow thermal conductivity of polymers.

The CoMFi is weaved into fabrics on a sample weaving machine (CCI Tech, Inc.). One of the challenges, in weaving the FIRST structure is to align the CoMFi monofilaments in the woven structure with minimum level of torque (or twist) about its axis. The inherent nature of processing (unwinding, etc.) of yarns into fabrics generally alter (add or remove) twist level in fibers. Particular care is taken to minimize the twisting of yarns during processing.

Finally, in order to enhance the sensory characteristics of FIRST, the potential of stimulating hydrophobic and hydrophilic behavior to parts of the FIRST for capacitive and wetness sensing, respectively, is applied through structural manipulation and application of surface finish, selectively. It should be noted that electrowetting properties of the texels can be used to absorb or repel fluids to bring analytes to the intersection for analysis and remove afterwards. When it is fabricated with a hydrophobic material only, the applied electric fields to CoMFi would cause electromagnetic forces to actuate the fibers and modulate the texel volume (the space at the intersection) and modify its wetting properties [Mugele, F., & Baret, J. C. (2005). Electrowetting: from basics to applications. Journal of Physics: Condensed Matter, 17(28), R705; Verplanck, N., Coffinier, Y., Thomy, V., & Boukherroub, R. (2007). Wettability switching techniques on superhydrophobic surfaces. Nanoscale Research Letters, 2(12), 577-596; Dufour, R., Dibao-Dina, A., Harnois, M., Tao, X., Dufour, C., Boukherroub, R., Senez, V. & Thomy, V. (2013). Electrowetting on functional fibers. Soft Matter, 9(2), 492-497; Lifton, V. A., & Simon, S. (2011). Preparation and electrowetting transitions on superhydrophobic/hydrophilic bi-layer structures. Journal of Porous Materials, 18(5), 535-544]. Therefore, electrowetting can be used to transport and capture bodily fluids in the pixel and repel it when the analysis is over. In another example, a hydrophilic material may be used. The hydrophobic and/or hydrophilic material may be applied to the entirety of the woven wires or a select portion of the woven wires. The portion may be selected if it is desired to prevent moisture from reaching one or more sensors in the selected portion.

Mechanical and Environmental Stability Characterization of CoMFi

Variable-pressure and low-voltage field-emission scanning electron microscopy (SEM) of the surface and cross-section of CoMFi and corresponding FIRSTs are routinely performed for quality control purposes regarding cross-sectional uniformity and semi-quantitative assessment of dispersion of particles in the conducting segments of CoMFi. Images of CoMFi and FIRST were collected in high-resolution digital format and analyzed to extract the geometrical features. As illustrated in FIG. 4, there are three different cross-sections for electrodes, capacitive tactile sensors, and impedance sensors for wetness. The electrode structures require more exposure of the conductive inner clad of the fiber to minimize the contact impedance with the skin to achieve biopotential sensing while these exposure openings would affect the performance of capacitive sensor structures if they get shorted in the presence of conductive fluids (i.e. urine or sweat). These three separate cross-sections provide knowledge on how to obtain a "uniform" CoMFi cross-section as illustrated in FIG. 2 that can achieve these three sensing capabilities simultaneously. A uniform CoMFi cross-section informs the design of analog front-end circuits interfacing electrodes and a more careful impedance analysis to differentiate tactile-force based capacitive changes from the moisture-based conductivity changes when the bodily fluids are present. It is noteworthy that the capability of distributed sensing from different parts of the patch and presence of computational processing platforms on-board are advantageous to mitigate the mentioned limitations imposed by a uniform CoMFi cross-section.

To understand CoMFi's mechanical (elastic modulus, etc.) and recovery behavior (hysteresis) from repeated deformation as a function of various design parameters, both CoMFi and FIRST are evaluated under cyclic strain of varying amplitude and frequency to emulate actual use. This is particularly important to be able to preserve the desirable "textile" characteristics while imparting the sensory function to the fabric substrate. During cycling, the stress-strain data is collected and subsequently analyzed for stress relaxation and hysteresis. After exposing the test sample to a predetermined number of cycles, the changes in its mechanical behavior as well as its morphology are studied to determine the extent of strain-induced degradation. Stress relaxation behavior of the materials are also examined to understand the effect of CNF content on molecular-level processes. Ohmic behavior of CoMFi before and after deformation (including cyclical) are determined over the current range used to measure electrical properties. Such measurements elucidate changes in conducting pathways as a result of applied strain. Changes in ohmic behavior may provide evidence of an altered percolating network due to damage sustained by the FIRST.

The deterioration of a sensor's mechanical and electrical performance as a function of exposure to a standard environment and elevated temperature and humidity conditions are considered by storing the CoMFi and FIRST in an environmental chamber for predetermined time intervals. Changes in mechanical and electrical behavior after and before exposure are considered and related to environmental conditions using empirical correlations or suitable models if available.

Finally, although a major advantage of the textile based production is its very low cost enabling disposable sensor patches, washing and reusing it to widen the application range are considered. The changes in sensory characteristics of FIRST resulting from detergent solution and abrasive action due to typical hand and home-machine launderings are considered. A standard test method is followed using a Lauder-Ometer that allows accelerated and representative simulation of washing, rinsing, and drying conditions (temperature, chemical environment, etc.) [Colorfastness to Laundering, Home and Commercial: Accelerated, AATCC Test Method 61-2004, Technical Manual of the American Association of Textile Chemists and Colorists, 2004, Research Triangle Park, NC]. Any loss in mechanical properties and sensory characteristics due to washing are evaluated. If mechanical agitation disturbs the CoMFi structure, only-chemical cleaning (such as soaking in isopropyl alcohol) may still be possible.

Characterization of the Sensing Behavior of CoMFi and FIRST

Computational Analysis: a computational model of FIRST based sensing system is developed using a finite element modelling (FEM) software (e.g., ANSYS) based on the range of possible conductivity and mechanical properties of CoMFi. An equivalent circuit model of the single texel (a network of resistances and capacitances) is built on ANSYS to assess its performance under tactile forces and when a conductive ionic liquid like urine or sweat is present within the texel (see FIG. 2). The tactile forces change the proximity of the warp (column) and filling (row) yarns along the thickness direction, thereby altering its capacitive properties. On the other hand, the change in the resistive characteristics of the impedance spectrum would reflect the presence of conductive medium (e.g., water) between the fibers (see FIG. 6).

The single texel analysis is extended to FIRST's woven structure made of monofilament yarns in along both warp and fill directions (FIG. 4). The initial design of interlacement of FIRST is a single, plain layer. Subsequent fabric structures include multiple layers, and basket or matt weave designs. A three dimensional array of texels where the fibers are woven into a fabric with multiple "stitched" layers is simulated, in which some of the fibers would traverse from one layer to another (FIG. 3). Several texels form between different rows and columns that can be addressed individually or in various parallel/series combinations. In addition to the single texels, the sensitivity, specificity and dynamic ranges of this distributed network of texels to monitor capacitive and impedance chances due to tactile forces and moisture is considered.

Figure 7:
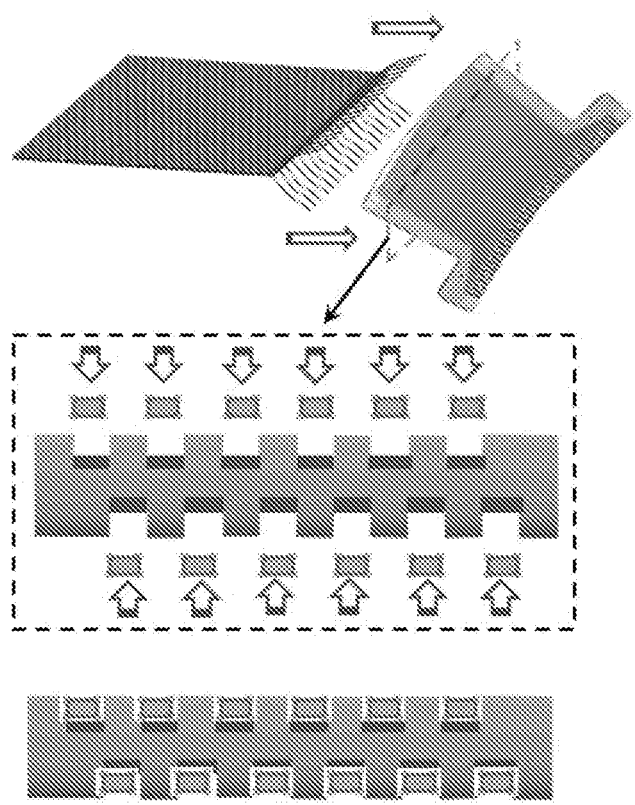
FIG. 7 a custom polyimide based flexible interconnect for assembly of fibers to electronic circuitry.

Characterization of Electrical Sensing Properties of FIRST: in order to connect the FIRST texels to electronic circuits, a flexible connector is microfabricated using patterned meander gold traces on polyimide substrate (FIG. 7). This connector enables easy connection of fiber ends (separated at the selvedge during weaving using appropriate weave design and/or yarn size) to the test circuits. In other constructions, a more robust and commercially available flexible cable and interconnect assembly can be used [Colorfastness to Laundering, Home and Commercial: Accelerated, AATCC Test Method 61-2004, Technical Manual of the American Association of Textile Chemists and Colorists, 2004, Research Triangle Park, NC].

The sensing strategy relies on measurement of small changes in the texel impedance/capacitance in order to detect the presence, and potentially the magnitude, of tactile forces and the moisture/wetness. This is achieved by electrochemical impedance spectroscopy (EIS) where a commercial-off-the-shelf (COTS) bench-top potentiostat is used initially and the plotted impedance spectrum is fitted to the equivalent circuit models to characterize the changes in capacitance and conductivity corresponding to the application of pressure and moisture, respectively. The inhomogeneity in initial values is calibrated and change in the model parameters with applied stimuli is analyzed. The results of these experiments and computational analysis are used to iteratively optimize the CoMFi and FIRST design parameters to obtain impedance values that can be measured by an electronic circuit while preserving the textile properties. It is noteworthy that with advanced EIS (higher impedance resolution and larger frequency range), dielectric spectroscopy and cyclic voltammetry (CV), it is possible to detect the content of the liquid (e.g., analyte content in bodily fluid) within the texel which requires relatively more complicated systems.

Figure 6:
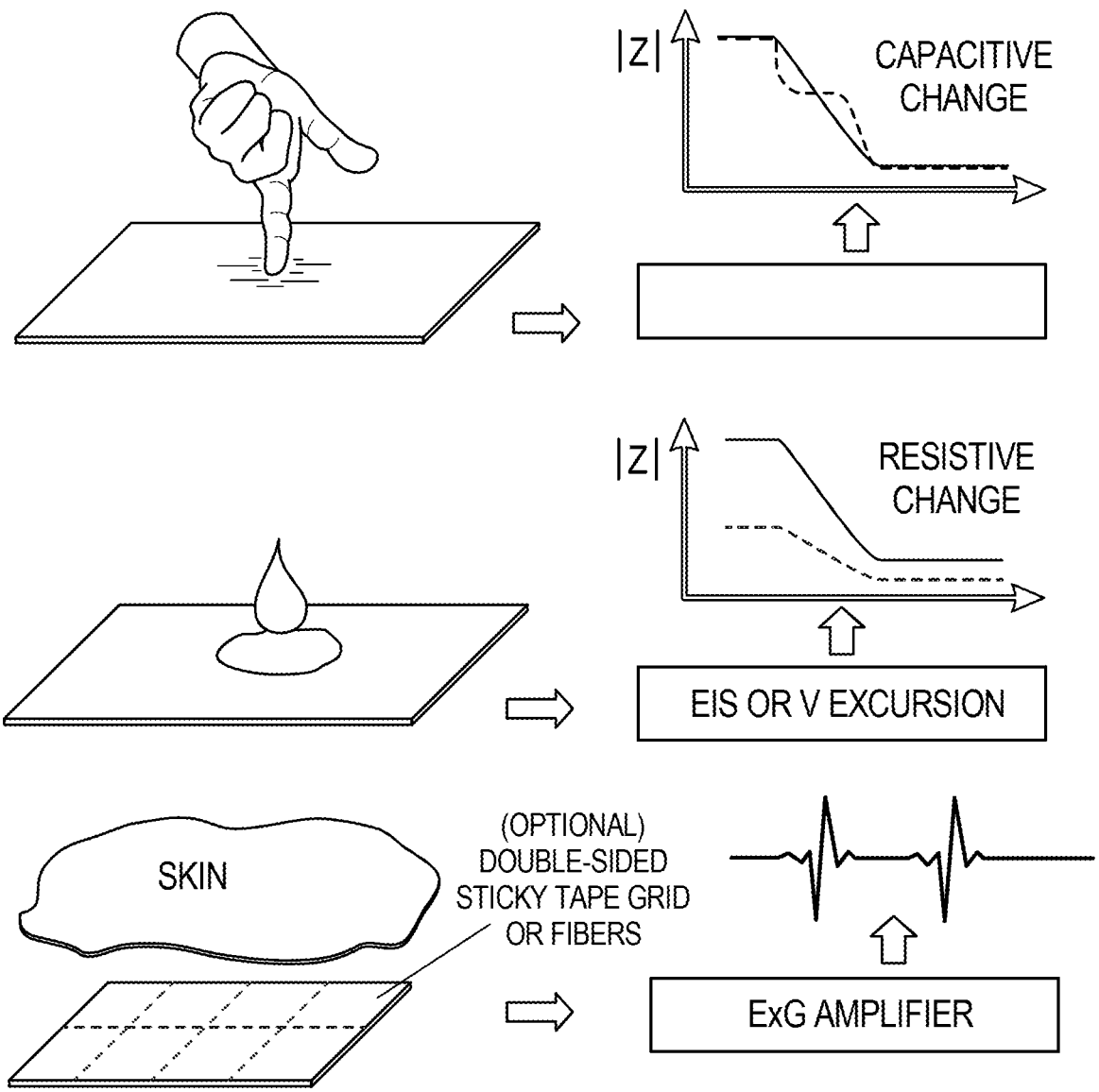
FIG. 6 illustrates representative changes in the impedance spectrum with applied pressure or with the presence of fluids between the fibers and the recorded ECG.

Though EIS holds great promise, given that the model includes a resistive capacitive network, a much simpler front-end circuit is used to assess the model parameter values depending on the application. For example, a Wheatstone bridge would rapidly provide the tactile force-dependent capacitance changes and voltage excursion studies would be used to extract moisture-dependent conductivity. For this, a simple current step is sent to the texel and the resulting voltage waveform is analyzed to calculate the relevant model parameters. The detection accuracies of EIS and these simpler solutions are also assessed and compared. Voltage excursion analysis would also enable a rapid assessment of ON/OFF response of the texels to the tactile forces and the moisture in the cases when it would be enough to detect just the presence of an extra pressure or wetness and map this presence across the distributed texel array. One inherent advantage of the CoMFi is the fact that almost its entire exposed surface can be designed to be conductive. This would enable the top layer of CoMFi based FIRST to act as an electrode to record biopotentials (e.g., ECG). To facilitate this further, the fibers in this outer layer are enhanced with long floats in fabric design. For a reliable mechanical contact, the fabric can be attached to the skin of the subject with a grid of double-sided medical-grade sticky tape (e.g., toupee tape with laser-cut rectangular openings) or sticky fibers weaved to the inner layer of the patch (FIG. 6).

Application-Specific-Integrated-Circuits Towards Smart CoMFi

The benchtop set-up described in the previous section may be bulky, slow and inappropriate for portable applications where multiple texels would be monitored rapidly. To address these issues, a circuit suitable for portability utilizes a CMOS based front-end circuit to route specific texels through multiplexers to an on-chip EIS system to analyze the impedance change. The detected value is converted to digital by means of the analog to digital converter (ADC), processed on a microcontroller/FPGA and transmitted wirelessly. The back-end of this system utilizes a COTS system-on-chip microcontroller with embedded Bluetooth transceiver to interface the electronic front-end circuit. The design of a custom microcontroller with a transmitter can be integrated on the same circuit.

The on-chip EIS platform measures the admittance of the texels in real time. The typical performance metrics are a supply voltage of 2V, frequency range of 0-10 kHz, power consumption of 10 mW, dynamic range 60 dB and overall area of 1×1 mm$^2$. The small size of this electronic circuit is helpful to preserve the flexibility of the overall system. A printed-circuit-board scale portable wireless electrochemical impedance spectrometer is also developed by connecting an impedance converter network analyzer such as Analog Devices (AD5933) to a system-on-chip such as TI cc2541. Despite its relatively higher power and large size, this system is suitable for substitution of a more complicated integrated circuit.

In parallel to the on-chip EIS system, a CMOS circuit is developed to enable on-chip voltage excursion analysis. A step current source can be used and record the resulting potential using the ADC of microcontroller. This is used to detect the equivalent circuit parameters more rapidly and using less power, though less accurately.

For ECG amplification, a low-noise amplifier is achieved by a Chopper amplifier including a feedback loop working at a frequency higher than the signal frequency to reduce the flicker noise at the output [Zhang, F., Mishra, A., Richardson, A. G., & Otis, B. (2011). A low-power ECoG/EEG processing IC with integrated multiband energy extractor. Circuits and Systems I: Regular Papers, IEEE Transactions on, 58(9), 2069-2082]. The gain of this amplifier is set to approximately 20 dB. In order to eliminate the upconverted noise of the Chopper amplifier and select the bandwidth of the signal, a low-pass Gm-C filter is used with a corner frequency of 100 Hz. A 50 nV/$\sqrt{Hz}$ input referred voltage noise density with above 120 dB common-mode-rejection-ratio (CMRR) is targeted for a current consumption of 50 µA at 2V supply voltage.

Testbed and Evaluation Platform

Each sensor type (biopotential, wetness, tactile) requires distinct optimization strategies based on the sensing modality and the application where it is deployed. The choice of measuring from one texel or from multiple texels in parallel, the mechanical and electrical properties of the insulating and conductive materials, the fiber cross-sectional and fabric weaving architectures are decided based on the contaminants and noise sources in the medium to achieve a practical and useful sensitivity, specificity and dynamic range. The desired impedance of the extruded ComFi and the woven texels are optimized while considering the "textile" properties and wearability of the fabric and easiness of its fabrication. Once the number and distribution of the texels are decided within the fabric and simulated in the computational FEM platform, interconnects and multiplexing mechanisms are designed to address each texel robustly and get the data to the processor. The nominal impedance range of the CoMFi is a major consideration when deciding upon the front-end circuit component values when recording the biopotentials, monitoring the capacitance for tactile sensing and assessing the impedance change for wetness detection. The final stage is deciding upon the sensor fusion algorithms to correlate the data coming from various sensors distributed through the fabric to extract the relevant biomedical information while eliminating the noise and undesired artifacts. The fusion algorithms are able to adapt the multiplexing scheme to read from other sensors if the current set is not efficient.

Figure 8:
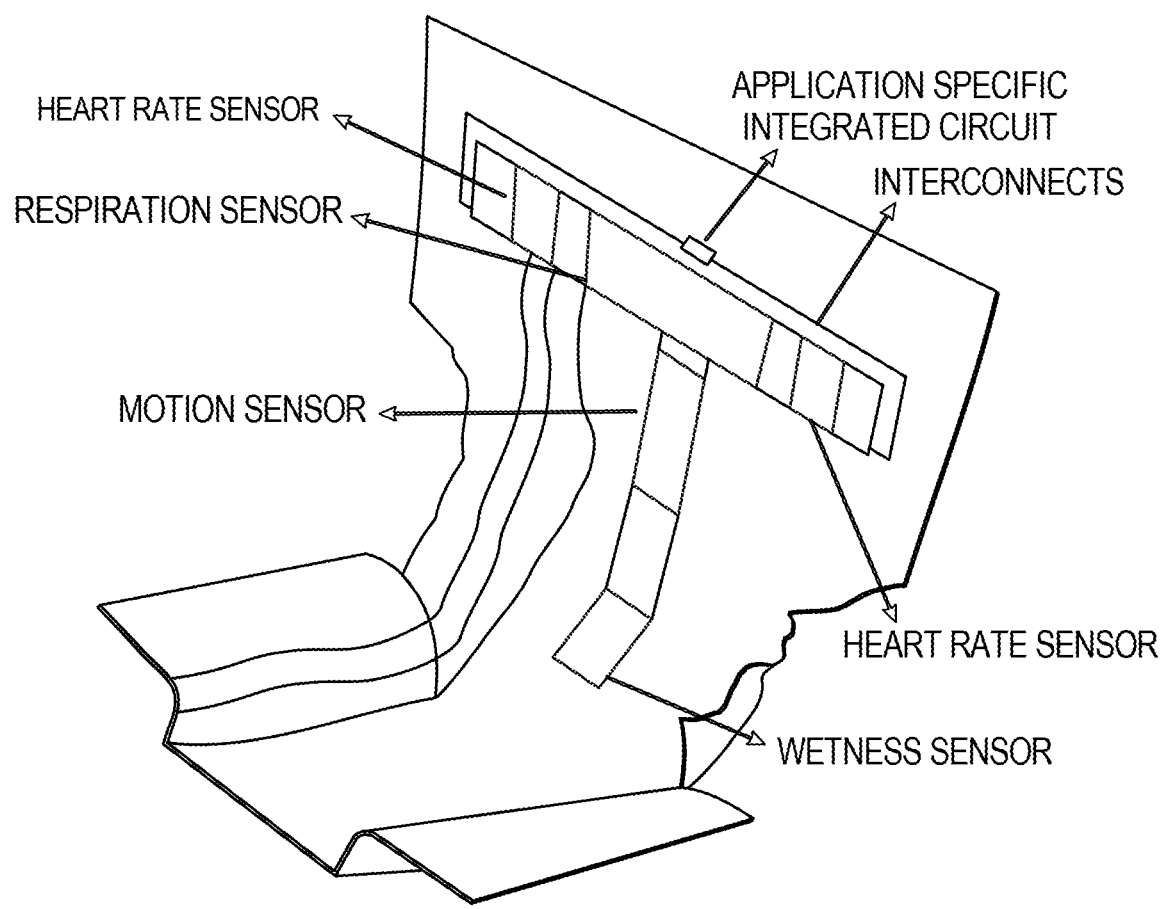
FIG. 8 illustrates a smart diaper concept using FIRST to measure physiological parameters. The circuit is connected to a COTS Bluetooth chip for wireless data transfer.

Under these design guidelines, as a technology demonstrator, the multi-component strand based FIRST is integrated into a diaper with the aim of critical health monitoring of infants in intensive care units and bedridden elderly (FIG. 8). The modular structure and very low cost production enable circuit systems to be reused with multiple diapers where the sensing FIRST part can be disposed with each diaper. The FIRST in the waistband part of the diaper is used to assess the tactile forces to detect respiratory rate and the movement of the patient. Although, the EIS or detailed voltage excursion analysis would enable the precise measurement of tactile forces, it would be sufficient to assess the ON/OFF response of the texels and count the number of texels turning on to monitor movement and the respiratory rate. The sensor texels in the waistband also record the ECG waves to monitor R-R interval for heart rate variability. The multi-component strand in the working part of the diaper is used to assess the wetness to record urination frequency and amount. A more advanced EIS and CV may be used to analyze the content of the urine; however, it will be used only for detecting the presence of bodily fluid. For this, the system analyzes the map of the texels that turn ON. On-chip computational processing is used to extract and compress information related to the respiratory rate and heart rate variability, movement and wetness. As mentioned earlier, in addition to the bodily fluid content detection, the other exciting potential capabilities that can be included in this testbed in the future are to detect the hydration levels based on skin/tissue impedance properties [Huang, X., Yeo, W. H., Liu, Y., & Rogers, J. A. (2012). Epidermal differential impedance sensor for conformal skin hydration monitoring. Biointerphases, 7(1), 52; Huang, X., Cheng, H., Chen, K., Zhang, Y., Liu, Y., Zhu, C., Ouyang, S. & Rogers, J. A. (2013). Epidermal impedance sensing sheets for precision hydration assessment and spatial mapping; Cheng, H., Zhang, Y., Huang, X., Rogers, J. A., & Huang, Y. (2013). Analysis of a concentric coplanar capacitor for epidermal hydration sensing. Sensors and Actuators A: Physical, 203, 149-153] and to use electrowetting to capture bodily fluids in the texel and repel it when the analysis is over [Mugele, F., & Baret, J. C. (2005). Electrowetting: from basics to applications. Journal of Physics: Condensed Matter, 17(28), R705; Verplanck, N., Coffinier, Y., Thomy, V., & Boukherroub, R. (2007). Wettability switching techniques on superhydrophobic surfaces. Nanoscale Research Letters, 2(12), 577-596; Dufour, R., Dibao-Dina, A., Harnois, M., Tao, X., Dufour, C., Boukherroub, R., Senez, V. & Thomy, V. (2013). Electrowetting on functional fibers. Soft Matter, 9(2), 492-497; Lifton, V. A., & Simon, S. (2011). Preparation and electrowetting transitions on superhydrophobic/hydrophilic bi-layer structures. Journal of Porous Materials, 18(5), 535-544].

Preliminary Prototype Developments

One of the key issues in the successful development of FIRST is the design of the percolative particle/polymer with high conductivity that can be extruded into fibers. FIG. 5 illustrates the design and development of flexible piezoresistive strain sensors using polymer nanocomposites composed of plasticized thermoplastic or a cross-linked elastomer and containing carbon nanofibers at concentrations just above the percolation threshold [Toprakci, H. A. K., Kalanadhabhatla, S. K., Spontak, R. J., Ghosh, T. K., "Polymer Nanocomposites Containing Carbon Nanofibers as Soft Printable Sensors Exhibiting Strain-Reversible Piezoresistivity," Adv. Funct. Mater., 23, 5536 (2013), doi: 10.1002/adfm.201300034]. The electrical conductivity of both composites were altered to maximize their sensory behavior.

Figure 1:
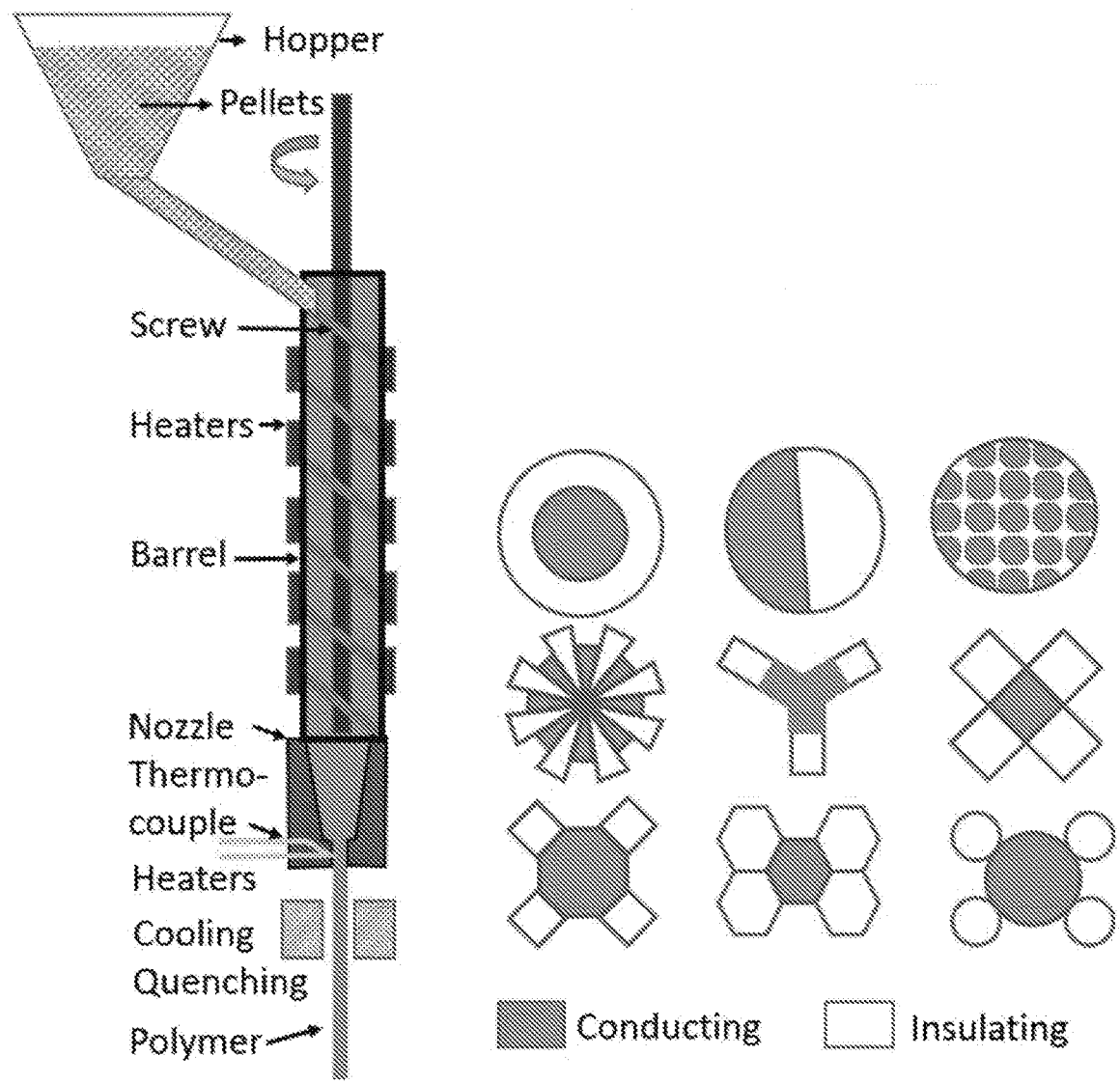
FIG. 1 illustrates a fiber extrusion process and sample multicomponent fiber cross-sections (top row: core-sheath, side by side, islands-in-a-sea; bottom two rows: cross-sections related to CoMFi).

A tricomponent fiber extrusion facility was used to extrude the multi-component strands (CoMFi), which is also used for fibers of many cross-sections as shown in FIG. 1. This set up is used with the necessary die assembly to obtain the cross-sectional shape of the multi-component strand.

For proof-of-concept of the sensor geometry on different scales, two prototypes were fabricated, tested and the results are further described below.

Textile-Based Sensors

Figure 9:
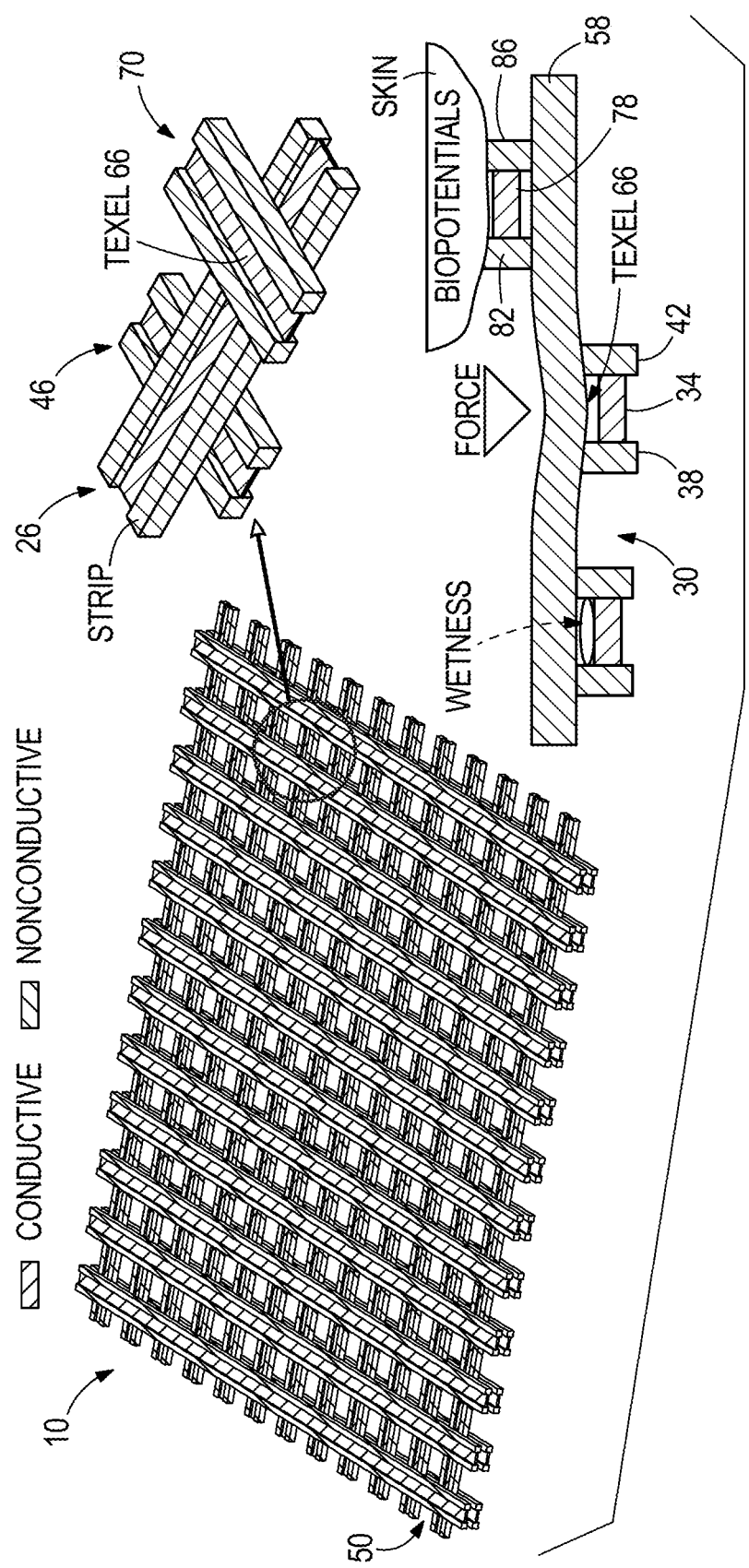
FIG. 9 is a pictorial representation of a sensing array and its operation principle according to an embodiment of the present invention.

FIG. 9 illustrates a potential configuration of a smart textile patch 10 according to an embodiment of the present invention. The patch in FIG. 9 does not illustrate the interlacement (up and down movement of one set of strands with respect to another orthogonal set of strands) between the sets of orthogonal multi-component strands for the sake of clarity. The potential interlacement patterns could be many. The smart textile patch 10 is a flexible array of sensors for concurrent tactile, biopotential, and wetness detection. In one construction, the textile patch 10 includes more than one layer of interlaced multicomponent strands. Each layer including at least two parallel sets of multi-component strands, with the possibility of having one common set of parallel multi-component strands between two layers. These layers are interlaced to form sensors at certain intersections of the multi-component strands. The two sets of orthogonal multi-component strands, shown in FIG. 9, include a first set 14 (illustrated as the top set) and a second set 18 (illustrated as the bottom set).

The first set of multi-component strands 14 includes a plurality of first multi-component strands 26. The multi-component strands 26 may comprise the same materials and operate in the same manner. In other constructions, some of the multi-component strands 26 may comprise different materials or combinations of materials and operate in a different manner than other first multi-component strands 26. In other constructions, all of the multi-component strands 26 may comprise different materials or combinations of materials and operate in a different manner from one another. The multi-component strands 26 are oriented parallel (in a general sense and a perfect parallel orientation is not required) to one another with a gap 30 separating each adjacent multi-component strand.

In the embodiment illustrated in FIG. 9, the first multi-component strands 26 comprise the same materials and operate in the same manner. The first multi-component strands 26 includes a base 34, a first leg 38 coupled to the base 34, and a second leg 42 coupled to the base 34 and positioned opposite the first leg 38. The first multi-component strand 26 forms what may be referred to as an "H" formation. The base 34 is comprised of material that is conductive while the first leg 38 and the second leg 42 are comprised of material that is non-conductive. For example, in some embodiments, the base 34 can comprise gold, and the first leg 38 and the second leg 42 can comprise polyimide.

The second set of multi-component strands 18 includes a plurality of second multi-component strands 46 or 70. The second set of multi-component strands 46 or 70 may comprise the same materials and operate in the same manner. In other constructions, some of the second multi-component strands 46 or 70 may comprise different materials or combinations of materials and operate in a different manner than other second multi-component strands 46 or 70. In other constructions, all of the second multi-component strands 46 may comprise different materials or combinations of materials and operate in a different manner from one another. The second multi-component strands 46 or 70 are oriented parallel (in a general sense and a perfect parallel orientation is not required) to one another with a gap 50 separating each adjacent multi-component strand.

In the embodiment illustrated in FIG. 9, the second set of multi-component strands 46 comprise the same materials and operate in the same manner. The second multi-component strands 46 include a base 54, a first leg 58 coupled to the base 54, and a second leg 62 coupled to the base 54 and positioned opposite the first leg 58. The second multi-component strands 46 form what may be referred to as an "H" formation. The base 54 is comprised of material that is conductive while the first leg 58 and the second leg 62 are comprised of material that is non-conductive. For example, in some embodiments, the base 54 can comprise gold, and the first leg 58 and the second leg 62 can comprise polyimide.

The multi-component strands 46 of the second set 18 are oriented orthogonal to each one of the multi-component strands 26 of the first set 14. The second multi-component strands 46 are "on top of" the first multi-component strands 26 thereby forming intersections 66 (or texels) where the second multi-component strands 46 are in contact with the first multi-component strands 26. These intersections 66 create a capacitor with two conductive layers (base 34 and base 54) separated by air as the dielectric material. When a force is applied to the textile patch 10, the patch flexes thereby changing the air gap and thus the capacitance. As a result, coupled capacitance of the patch 10 can be used to estimate the presence and the value of an applied force.

The intersections 66 also can detect wetness such as sweat from human skin. At the intersections 66, the space between the two conductive sets (base 34 and base 54) normally filled with air can become two parallel capacitive-resistive pairs when the space fills (partially or completely) with fluid. When the space fills (partially or completely) with fluid, the intersection no longer forms a capacitor as described above, but rather becomes two parallel capacitive-resistive pairs connected by a resistive element (due to the metal-electrolyte interface). The resulting impedance change can be sensed through impedance spectroscopy to determine the presence and salinity of the fluid.

In the embodiment illustrated in FIG. 9, one of the multi-component strands 70, belonging to the second set 18 comprise the same materials and operate in the same manner. The multi-component strands 70 include a base 78, a first leg 82 coupled to the base 78, and a second leg 86 coupled to the base 78 and positioned opposite the first leg 82. The multi-component strands 70 form what may be referred to as a "Π" formation since the base 78 is at the top (or same level) as the top of the first leg 82 and the second leg 86. The base 78 is comprised of material that is conductive while the first leg 82 and the second leg 86 are comprised of material that is non-conductive. For example, in some embodiments, the base 78 can comprise gold, and the first leg 82 and the second leg 86 can comprise polyimide.

The strand 70 or strand 46 of the second set 18 is oriented orthogonal to each one of the multi-component strands 26 of the first set 14. The choice of strand type 70 or 46 depends on the type of sensor patch being fabricated. The strand type 70 may be used as electrodes with exposed conductive area for contact with a surface (e.g., human skin) due to the "Π" formation. The "Π" formation provides more exposed conductive plates for better contact with the surface for biopotential detection with appropriate circuitry coupled thereto.

Figure 10:
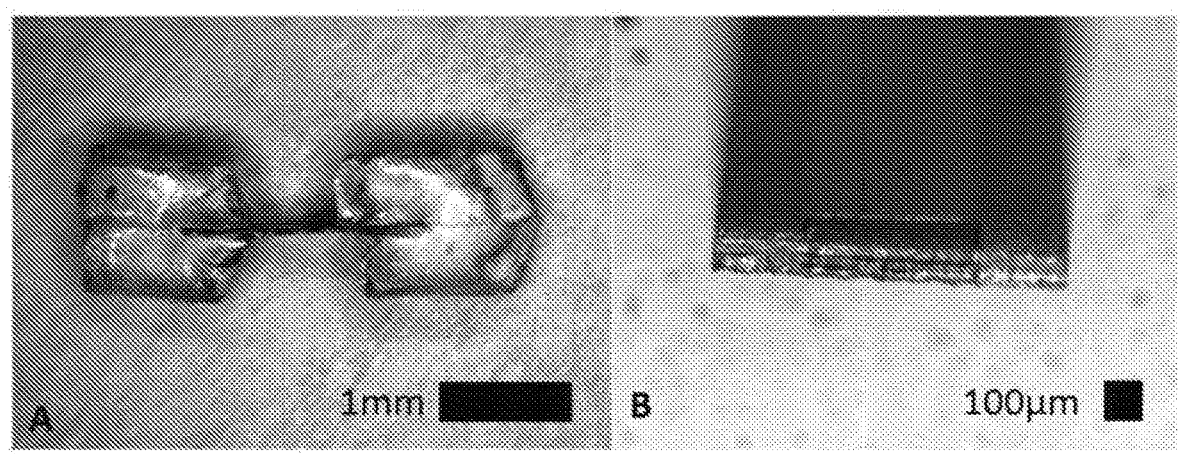
FIG. 10 illustrates enlarged cross-sectional views from a A) macro-strip and a B) micro-strip.
Figure 11:
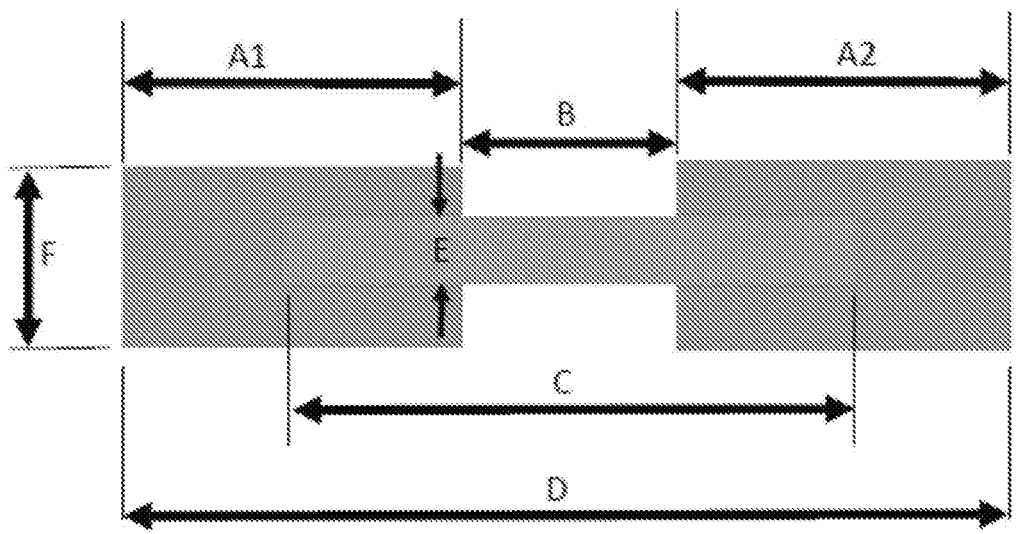
FIG. 11 illustrates exemplary dimensions for a macro-strip.

Two prototypes of the smart textile patch 10 were developed and fabricated. A first prototype was based on a macro-array scale, and a second prototype was based on a micro-array scale (width: 0.4 mm) to demonstrate scalability of the smart textile patch 10. In the first prototype, macro-strips (width: 4 mm) were assembled using copper etched into narrow rectangular stripes in printed circuit board (PCB) etchant as the conductor and clear 3M VHB tape shaped with a laser cutter into hollow rectangles as non-conductive spacers (see FIG. 10). A 2×2 macro-array was constructed by soldering macro-strips onto a printed circuit board into a three-layer array. In one construction, the macro-strip can have the dimensions as illustrated in FIG. 11. In other constructions, the macro-strip can have other dimensions such as approximately 0.5 mm to approximately 1.5 mm for A1 and A2, approximately 0.5 mm to approximately 1.5 mm for B, approximately 1 mm to approximately 2 mm for C, and approximately 2.5 mm to approximately 3.5 mm for D; for layer thickness, the macro-strip can have other dimensions such as approximately 0.1 mm to approximately 0.3 mm for E and approximately 0.5 mm to approximately 1.5 mm for F.

Figure 12:
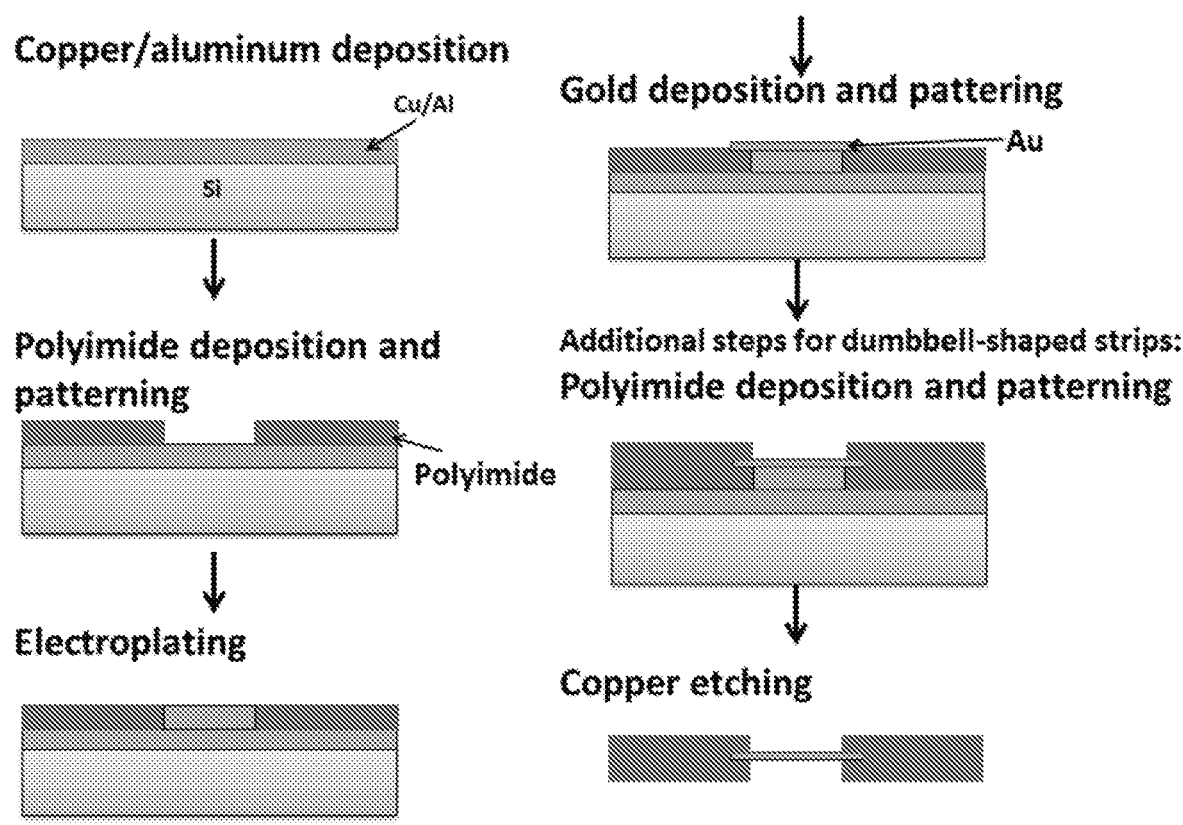
FIG. 12 illustrates a simplified microfabrication process flow for a micro-strip.
Figure 13:
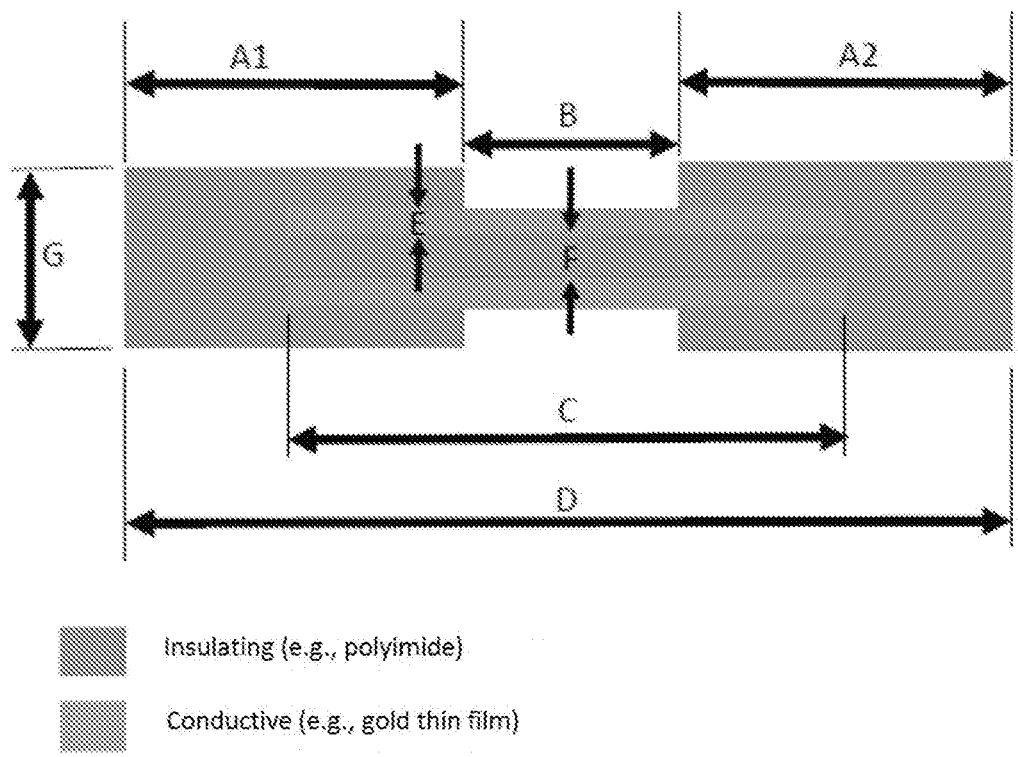
FIG. 13 illustrates exemplary dimensions for a micro-strip.

In the second prototype, a micro-sized version of the smart textile patch 10 was constructed using cleanroom based microfabrication techniques. FIG. 12 illustrates a simplified process flow used to create the micro-array. Micro-strips (width: 0.4 mm) were assembled and utilized gold as a conductor for its low resistivity and polyimide as non-conductive flexible spacers (see FIG. 10). The micro-array was assembled by layering a fabricated matrix of micro-strips and bonding the layers together by using adhesive. In one construction, the micro-strip can have the dimensions as illustrated in FIG. 13. In other constructions, the micro-strip can have other dimensions such as approximately 125 µm to approximately 175 µm for A1 and A2, approximately 25 µm to approximately 75 µm for B, approximately 125 µm to approximately 175 µm for C, and approximately 325 µm to approximately 375 µm for D; for layer thickness, the micro-strip can have other dimensions such as approximately 0.1 µm to approximately 0.3 µm for E, approximately 0.5 µm to approximately 2.5 µm for F, and approximately 11 µm to approximately 14 µm for G.

Figure 14:
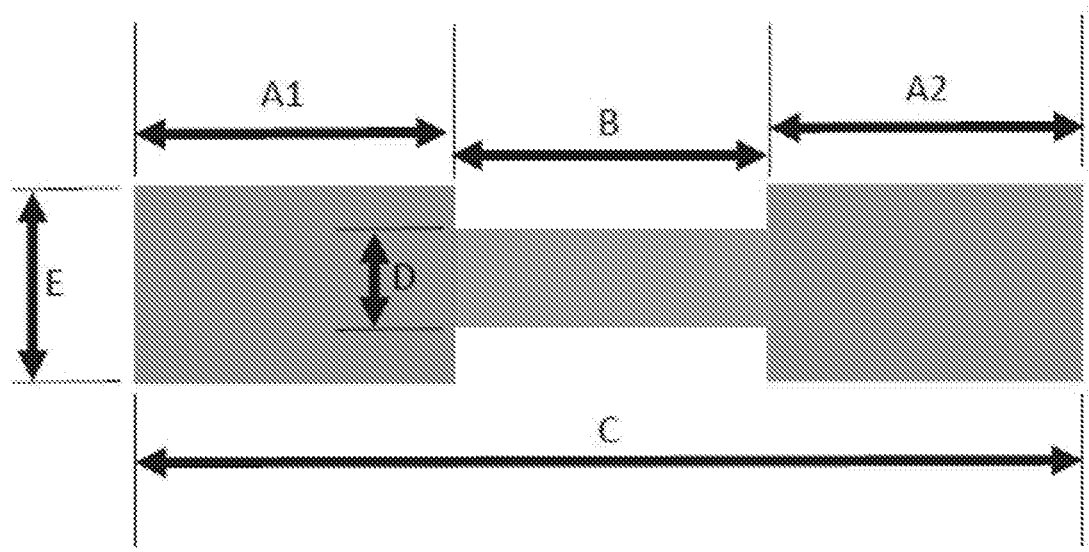
FIG. 14 illustrates exemplary dimensions for a textile fiber-based multi-component strand.

In a construction utilizing textile fibers, the multi-component strand can have the dimensions as illustrated in FIG. 14. In other constructions, the textile fiber-based strand can have other dimensions such as approximately 75 µm to approximately 125 µm for A1 and A2, approximately 75 µm to approximately 125 µm for B, and approximately 275 µm to approximately 325 µm for C; for layer thickness, the textile fiber-based strand can have other dimensions such as approximately 15 µm to approximately 25 µm for D and approximately 35 µm to approximately 45 µm for E. In some constructions, the textile fiber is nylon, but in other constructions, the textile fiber can be of any man-made fiber type (e.g. polyester, polyporopylene, etc.). The conducting part of the fiber may be made of any inherently conducting polymer or a polymer composite.

Figure 15:
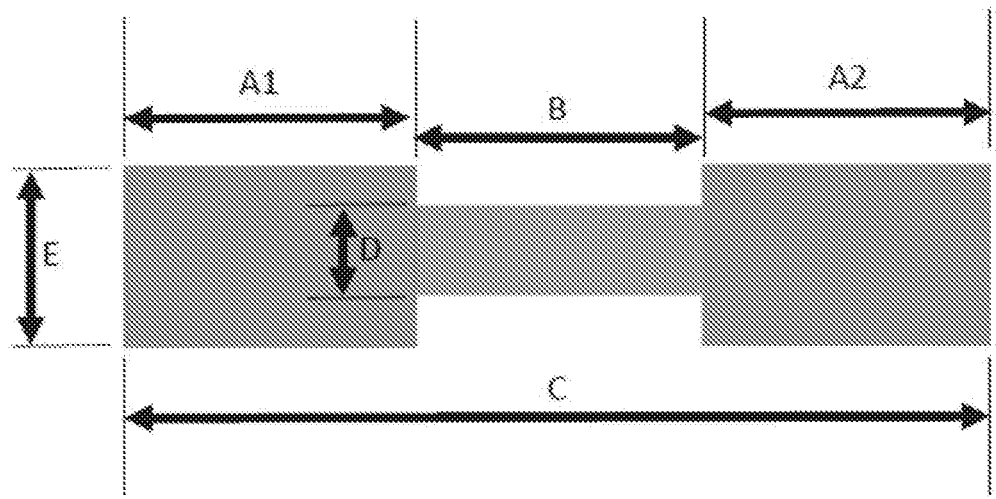
FIG. 15 illustrates exemplary dimensions for a 3D printed multi-component strand.

In a construction utilizing 3D printing techniques, the multi-component strand can have the dimensions as illustrated in FIG. 15. In other constructions, the 3D printed multi-component strand can have other dimensions such as approximately 200 µm to approximately 300 µm for A1 and A2, approximately 200 µm to approximately 300 µm for B, and approximately 700 µm to approximately 800 µm for C; for layer thickness, the 3D printed multi-component strand can have other dimensions such as approximately 350 µm to approximately 450 µm for D and approximately 750 µm to approximately 850 µm for E.

The first and second prototypes of the smart textile patch 10 were connected to an electronic circuit 90 configured to acquire and analyze signals from the tactile and wetness sensors formed at the intersections 66 (a texel) formed by the first multi-component strands 26 and the second multi-component strands 46 and the biopotential sensors formed at the intersections (a texel) formed by the first multi-component strands 26 and the second multi-component strands 70.

Figures 16A, 16B:
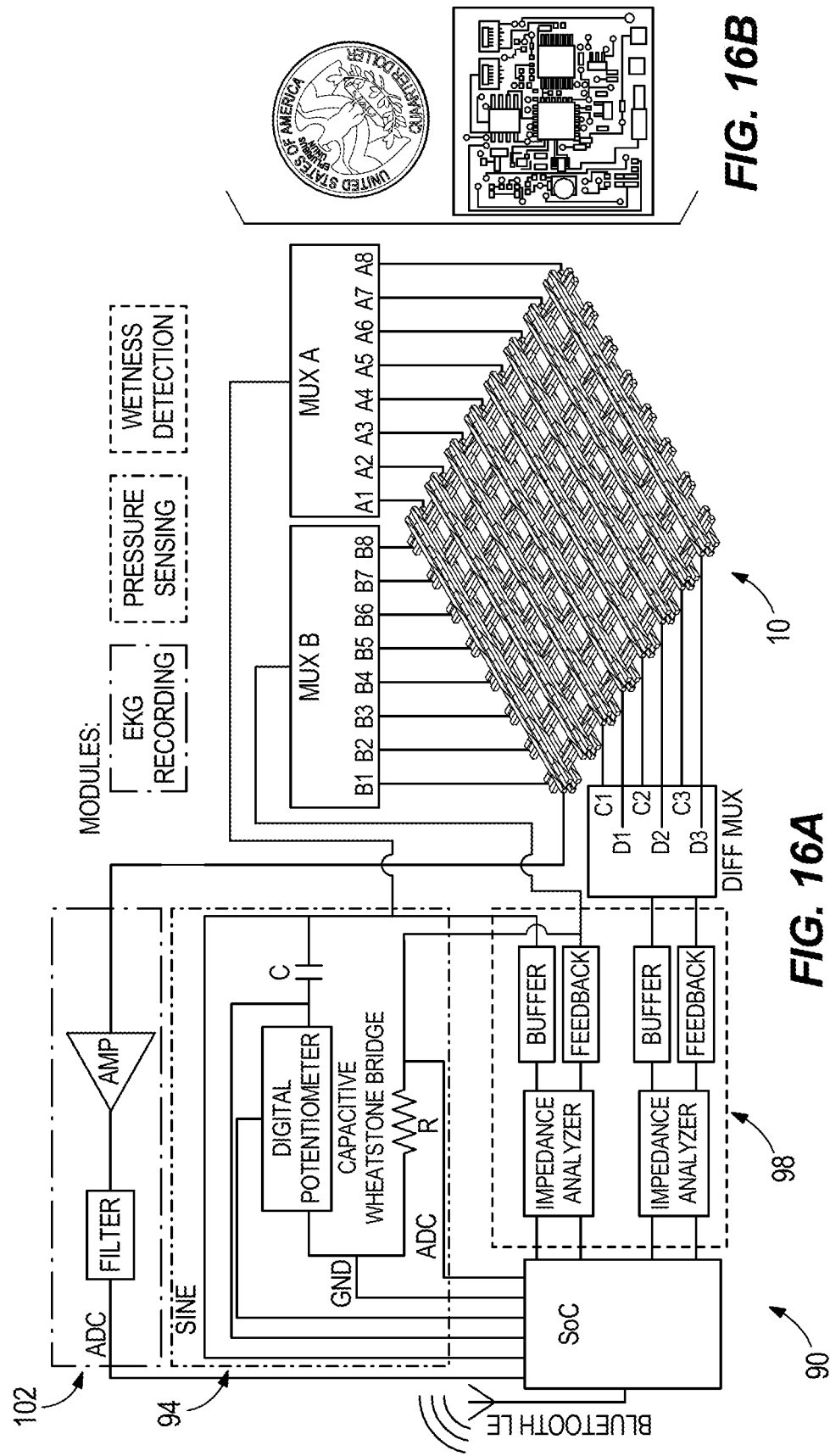
FIG. 16 illustrates (A) an electronic schematic for a wearable sensing and wireless data delivery system and (B) an actual circuit without arrays.
Figure 17:
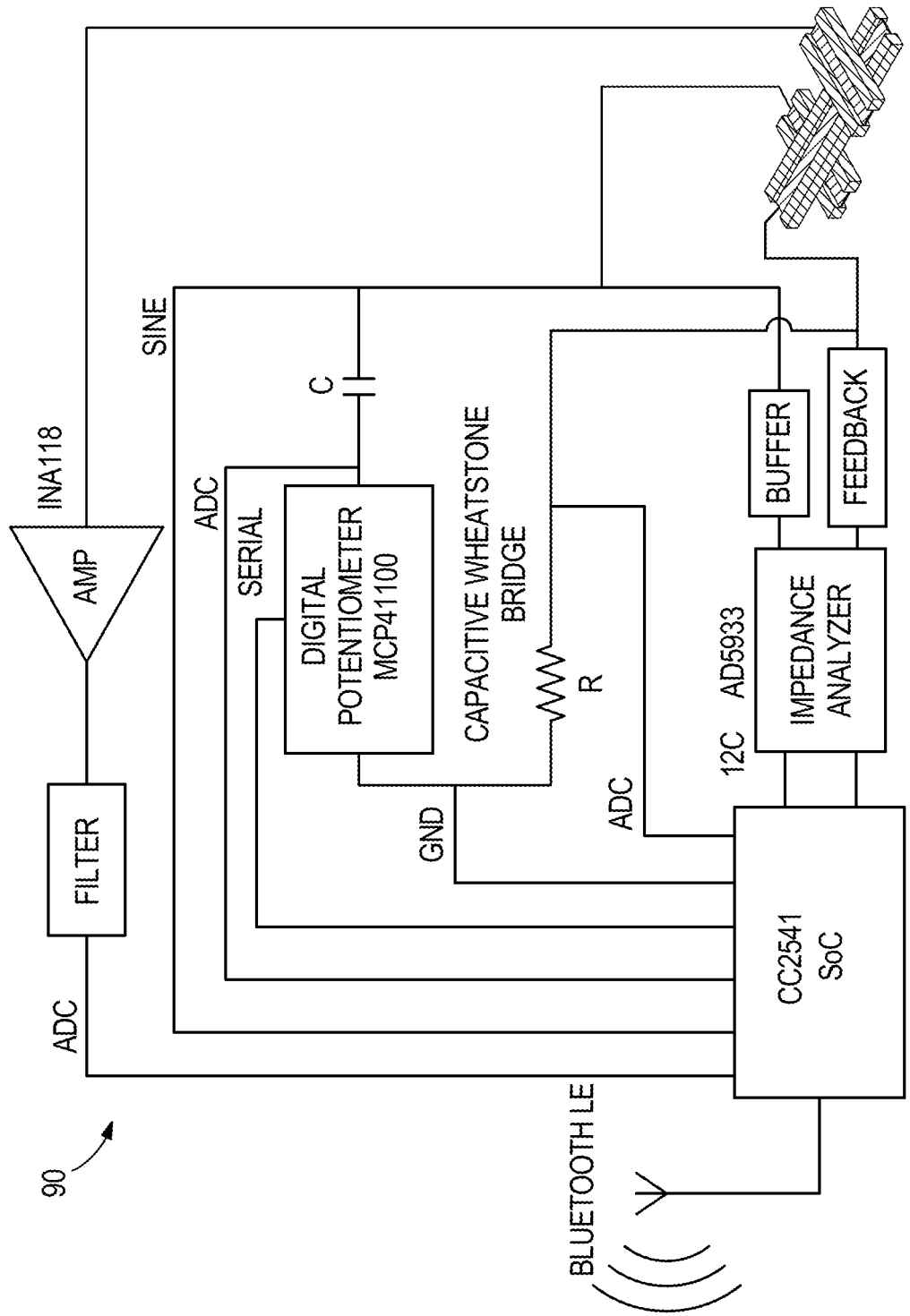
FIG. 17 illustrates an enlarged electronic schematic for a wearable sensing and wireless data delivery system.

With reference to FIGS. 16 and 17, the circuit 90 comprises three circuits. The first circuit 94 is a Wheatstone bridge to detect small capacitance changes in tactile sensing. The second circuit 98 utilizes an impedance analyzer chip (e.g., AD5933 from Analog Devices) to characterize impedance in wetness detection. The third circuit 102 is enabled using an instrumentation amplifier (e.g., INA118 from Texas Instruments) and additional signal amplification circuitry for detecting biopotentials such as an ECG. These three circuits 94, 98, 102 were merged and miniaturized into a wearable sensing and wireless data delivery system (e.g., Bluetooth) for ease of incorporation in biomedical and textile applications (see FIG. 16). The circuit 90 can be further miniaturized with a more dense PCB layout.

Testing was done on single texels by applying forces using Chatillon® DFS II force gauge attached to a stepper-motor-controlled stand. Wetness detection was implemented by applying several concentrations of saline solution onto the texel. ECG recording was tested using three texels as electrodes on the chest. For macro- and micro-texels, plots of capacitance change against applied force, linear decrease in 1 kHz impedance with increasing saline concentration and ECG recordings were shown in FIG. 18. As expected, the capacitance plateaued after a certain amount of force as the compression limits were approached. When saturated or with same amount solution, texels were able to differentiate salinity of the solution. The ECG potentials were similar for both prototype sizes.

Figure 18:
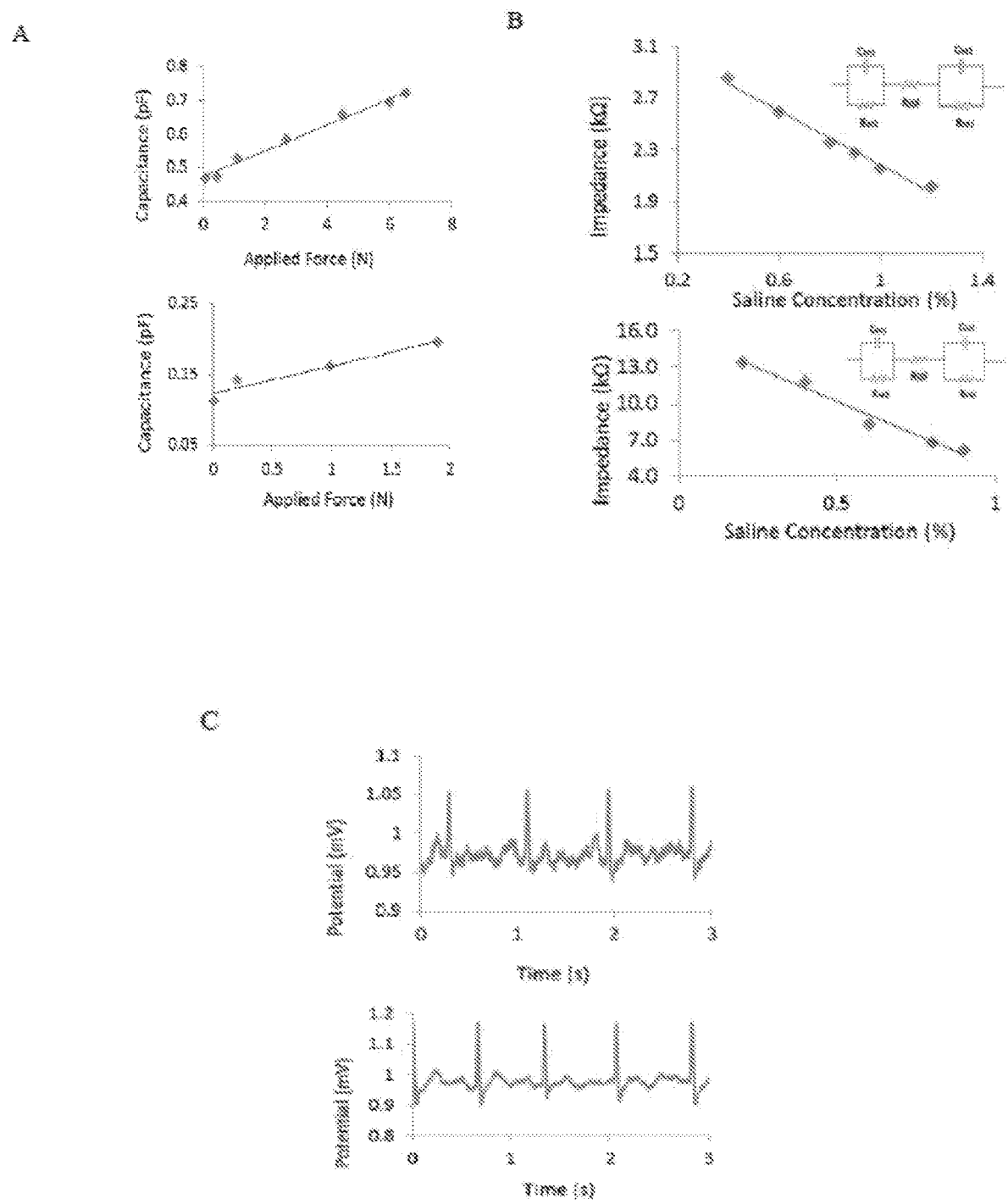
FIG. 18 graphically illustrates (A) capacitance change with force application, (B) impedance at 1 kHz for different saline concentrations (Rsol) for wetness detection and salinity measurement, and (C) ECG recordings on chest. For all cases macro-texel is presented on the top and microtexel in the bottom.

The results for tactile sensing are shown in FIG. 18A. Plots of capacitance change against applied force for macro-texel and micro-texel are shown in FIG. 18A. The capacitance increases proportionally with increasing applied force for both macro-texel and micro-texel. As expected, the capacitance seemed to plateau after a certain amount of force is applied, with further increase in force causing minimal compression of flexible stripes and reduced change in capacitance for both prototypes (not shown in FIG. 18). Each size scale responds linearly to a different range of applied force.

Figure 19:
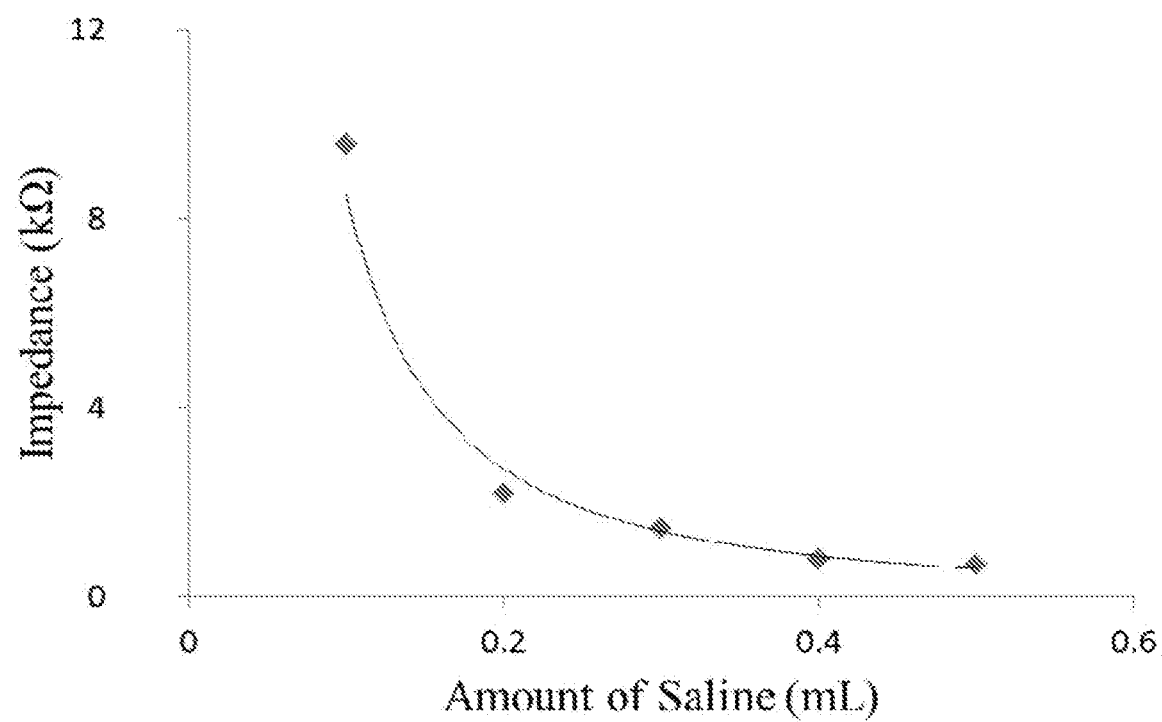
FIG. 19 is a graphical illustration of macro-texel impedance at 1 kHz for different amounts of 1% saline solution.

The results for wetness detection are shown in FIG. 18B, which displays the impedance of macro-texel and micro-texel at 1 kHz at different saline concentrations. Both texels show a linear decrease in impedance with increasing saline concentration. Here, the amount of saline solution used is important. When saturated or with the same amount of solution, texels can differentiate salinity of the solution. On the other hand, impedance change cannot be used to associate with salinity of the solution when different amounts of solution are used for testing. In this case, impedance changes are indicative of the amount of solution being used, as shown in FIG. 19.

The results for biopotential detection are shown in FIG. 18C. ECG recordings using micro-strips and macro-strips are shown in FIG. 18C. The peak potentials for both prototypes are very similar to each other. Since no additional material has been employed at the electrode-skin interface, micro-strips and macro-strips may need to be strapped to the chest during testing to ensure contact with skin for ECG recording.

Paper-Based Sensors

In another embodiment, the invention provides screen-printed sensors on folded paper substrates for multi-modal sensing of biopotentials, wetness, and pressure. As described above, these sensors contain three layers of sensing strips forming a 16-texel array where various layers are utilized for different sensing modalities. The unique cross-sectional geometry of the sensors enables the concurrent detection of tactile forces, biopotentials, and wetness.

The sensing capability of this sensor concept as described above uses manually assembled mm-scale and cleanroom fabricated micro-scale prototypes to be integrated into textiles. In this embodiment, fabrication of the sensors utilizes paper as a substrate. An example of this embodiment is incorporated into a diaper for critical health monitoring.

Paper has been used as a substrate for flexible and foldable electronics [A. C. Siegel, S. T. Phillips, M. D. Dickey, N. Lu, Z. Suo, and G. M. Whitesides, "Foldable printed circuit boards on paper substrates," *Adv. Funct. Mater.*, vol. 20, pp. 28-35, 2010]. It is a commonly available and an inexpensive resource and comes in a variety of different compositions with various material properties. Different papers can readily absorb moisture at various rates which has led to their widespread use in low cost microfluidic applications for performing bioassays and electrochemical sensing for diagnostics [A. W. Martinez, S. T. Phillips, M. J. Butte, and G. M. Whitesides, "Patterned paper as a platform for inexpensive, low-volume, portable bioassays," *Angew. Chemie—Int. Ed.*, vol. 46, pp. 1318-1320, 2007; Z. Nie, C. a Nijhuis, J. Gong, X. Chen, A. Kumachev, A. W. Martinez, M. Narovlyansky, and G. M. Whitesides, "Electrochemical sensing in paper-based microfluidic devices," *Lab chip*, vol. 10, no. c, pp. 477-483, 2010; A. W. Martinez, S. T. Phillips, G. M. Whitesides, and E. Carrilho, "Diagnostics for the developing world: Microfluidic paper-based analytical devices," *Anal. Chem.*, vol. 82, no. 1, pp. 3-10, 2010]. Paper has also been used to produce dermal patches for monitoring wound oxygenation [P. Mostafalu, W. Lenk, M. Dokmeci, B. Ziaie, A. Khademhosseini, and S. Sonkusale, "Wireless Flexible Smart Bandage for Continuous Monitoring of Wound Oxygenation," pp. 3-6, 2014; Rahimi, R., Chitnis, G., Mostafalu, P., Ochoa, M., Sonkusale, S., & Ziaie, B., "A low-cost oxygen sensor on paper for monitoring wound oxygenation," in *7th Int. Conf. Microtechnol. Med. Biol.*, Marina del Rey, Calif., 2013]. Paper substrates provide inherent flexibility and conformability making them well-suited for wearable healthcare applications. The extremely low cost of paper also makes it ideal for medical devices which come in contact with bodily fluids, because it can be easily incinerated and produced as a medical consumable or disposable [A. C. Siegel, S. T. Phillips, M. D. Dickey, N. Lu, Z. Suo, and G. M. Whitesides, "Foldable printed circuit boards on paper substrates," *Adv. Funct. Mater.*, vol. 20, pp. 28-35, 2010].

Figure 20:
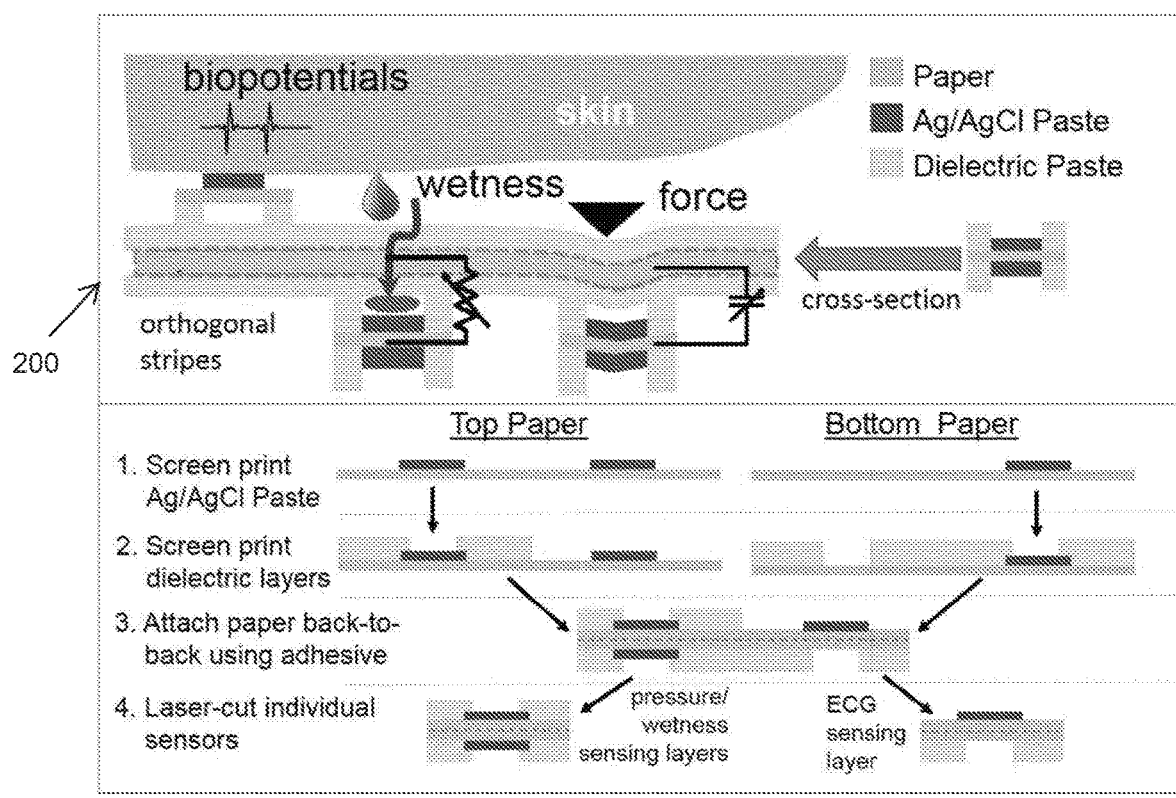
FIG. 20 is a pictorial representation of (top) a sensor array (top) for multi-modal sensors and (bottom) a fabrication method for screen-printed paper sensors.
Figure 21A:
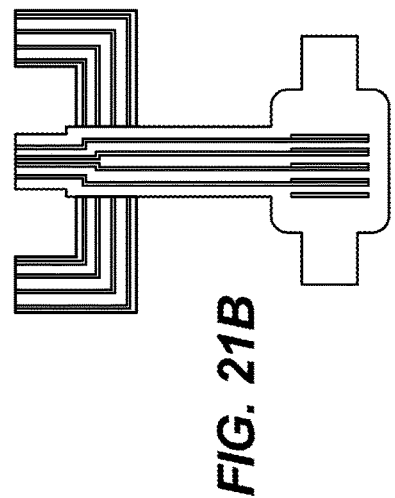
FIG. 21 illustrates a paper-sensor (A) unfolded, (B) folded, (C) unfolded sensor showing cross-section line, (D) description of folded sensor cross-section (E) cross-section of single texel.
Figure 21B:
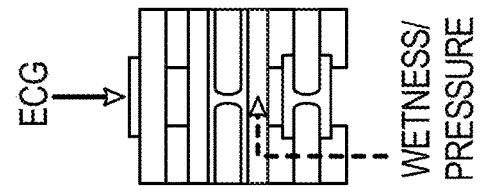
Figure 21C:
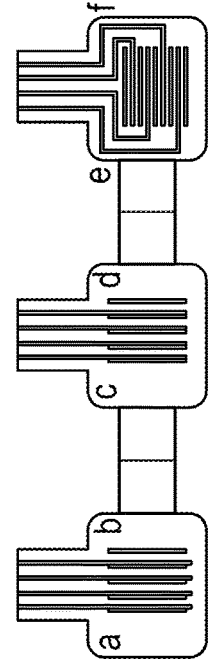
Figure 21D:
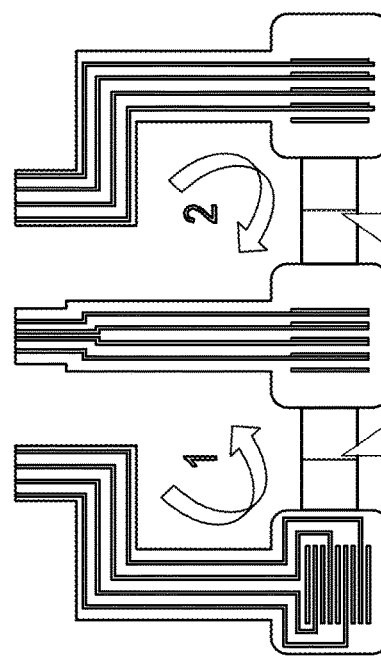
Figure 21E:
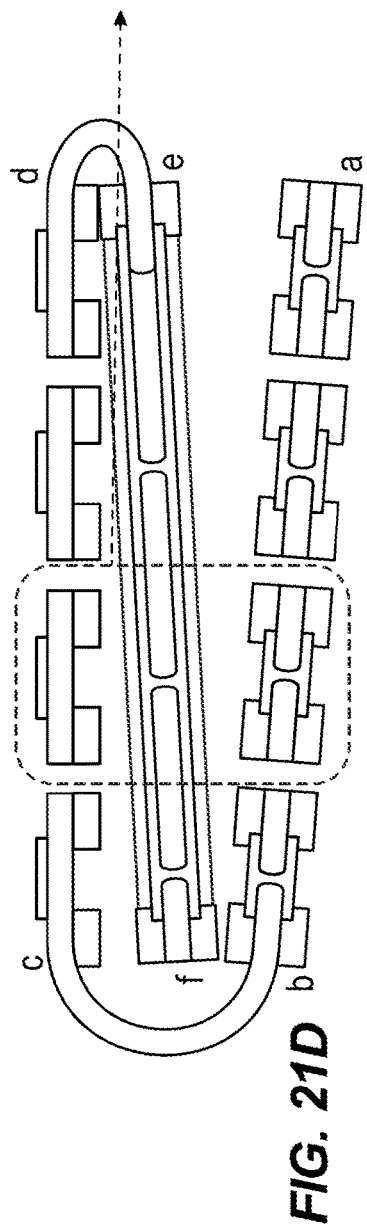

FIG. 20 illustrates a smart patch 200 according to an embodiment of the present invention. The smart patch 200 is a flexible array of sensors for concurrent tactile, biopotential, and wetness detection. FIG. 20 further illustrates a unique orthogonal structure of paper strips where the crossover of each row and column of strips, defined as a sensor "texel", operate to sense three physiologically relevant parameters. As similarly described above with the textile patch 10, the capacitance of a texel is used to detect applied tactile forces and the impedance of a texel is used to detect the presence of moisture and wetness. The exposed conducting layers of the strips are used as surface electrodes to record biopotentials.

In one example, the texels are distributed across the inner surface of a diaper for multimodal sensing. The texels in the waistband portion of the diaper are used to assess the tactile forces to determine respiratory rate and movement of the subject. The electrode texels in the waistband of the diaper record the ECG waves to monitor the R-R interval for heart rate variability. The sensors in the "working" part of the diaper are used to assess wetness to record urination frequency and amount. The low manufacturing cost of the paper sensors makes them disposable and potentially recyclable.

Figure 22:
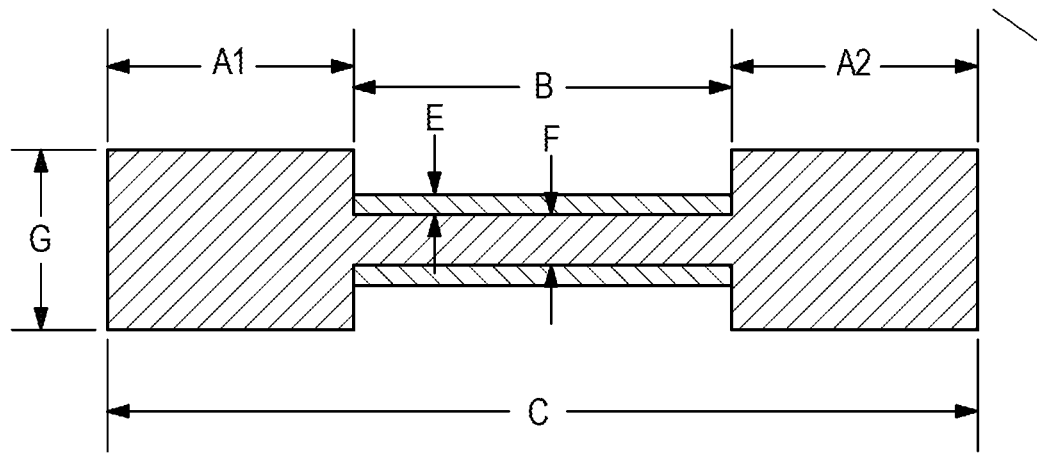
FIG. 22 illustrates exemplary dimensions for a paper-based multi-component strand.

The paper-based sensors were developed using conventional screen printing techniques as shown in FIG. 20. AGCL-675 paste (Conductive Compounds, Inc.) was used to produce the conductive traces and UV-10065 paste (Conductive Compounds, Inc.) was used as an insulation layer. The sensor layers were designed using Adobe Illustrator and corresponding patterns were printed using wax onto an Apollo laser transparency film. These transparencies were used for patterning capillary film on pre-stretched steel screens with a 250 mesh size (Sefar, Inc.). The sensor pattern was printed onto ITW Texwipe cleanroom paper. Two layers were aligned back to back and attached using Spray Adhesive (Elmer's Products, Inc). The sensors were patterned using the VLS3.60 laser cutter (Universal Laser Systems). The patterned sensors were then folded at two laser-cutter patterned perforations to produce a single sensing array having 16 sensing texels in a 4×4 array on three layers (FIG. 21) where each texel had an area of 7×7 mm$^2$. Each sensor includes three sets of terminal pads that fit to flexible printed circuit (FPC) connectors on the electronic circuit board for data acquisition and transmission. In one construction, the micro-strip can have the dimensions as illustrated in FIG. 22. In other constructions, the paper-based strip can have other dimensions such as approximately 75 μm to approximately 125 μm for A1 and A2, approximately 175 μm to approximately 275 μm for B, and approximately 375 μm to approximately 475 μm for C; for layer thickness, the paper-based strip can have other dimensions such as approximately 0.1 μm to approximately 0.5 μm for E, approximately 50 μm to approximately 110 μm for F, and approximately 175 μm to approximately 275 μm for G.

Figure 23:
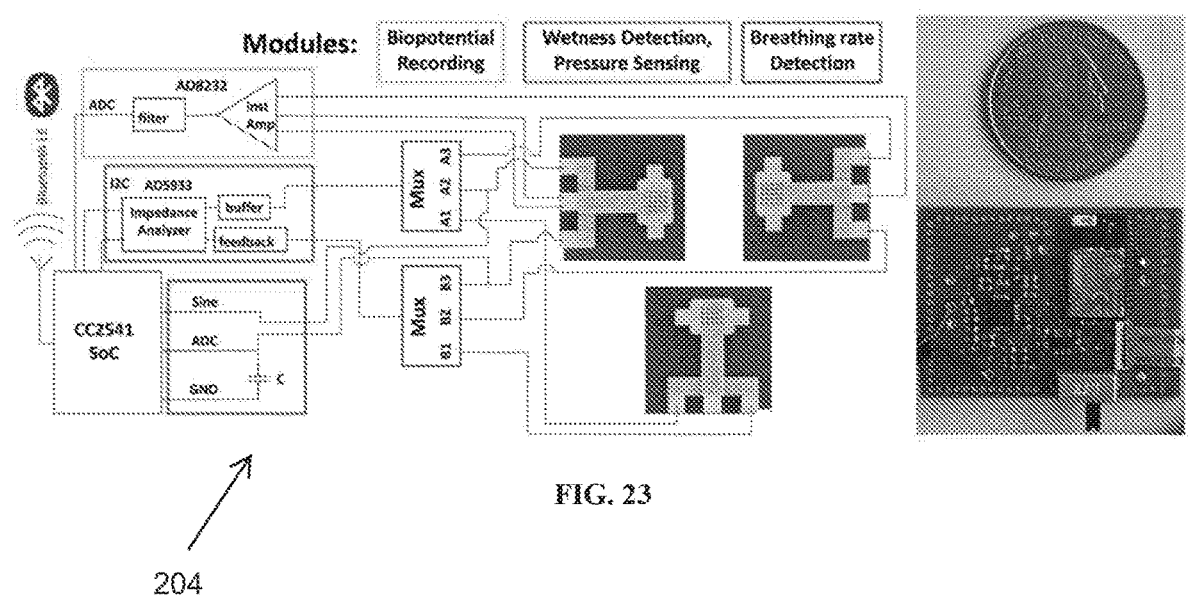
FIG. 23 is a block-diagram of a wireless interface and data acquisition circuit for paper sensors, and a fully assembled PCB.

FIG. 23 illustrates an electronic circuit 204 configured to acquire and analyze signals from the pressure/tactile and wetness sensors and biopotential sensors. A wireless system based on the Bluetooth Low Energy enabled Texas Instruments system-on-chip CC2541 was designed to acquire the data and transmit it wirelessly to a nearby data aggregator (a smartphone or computer) for further analysis. Two strategies were used for sensing tactile forces (capacitance) and wetness (impedance). For a more detailed quantitative assessment, AD5933 (Analog Devices) was utilized to perform impedance spectroscopy in order to determine the dielectric constant or impedance changes of the affected texels in the sensor array and correlate these changes to the applied forces and the presence of liquids within the texel. For a simpler qualitative tracking of the impedance change to assess the presence of wetness or motion and to calculate the respiratory rate, a capacitive/resistive divider circuit with the sensing element was implemented. The change in the voltage traces at this divider circuit was correlated with the application of forces related to motion and respiration and introduction of the liquid ionic solution such as urine. As for the biopotential detection, AD8232 (Analog Devices) was employed to detect the ECG signal using a 3-lead electrode configuration (FIG. 23). When integrated on a printed circuit board, the size of the overall circuit is 2.5×3 cm$^2$. The power consumption is about 40 mW and the typical battery duration is 37 hours with a 400 mAh Li-ion battery.

Figure 24:
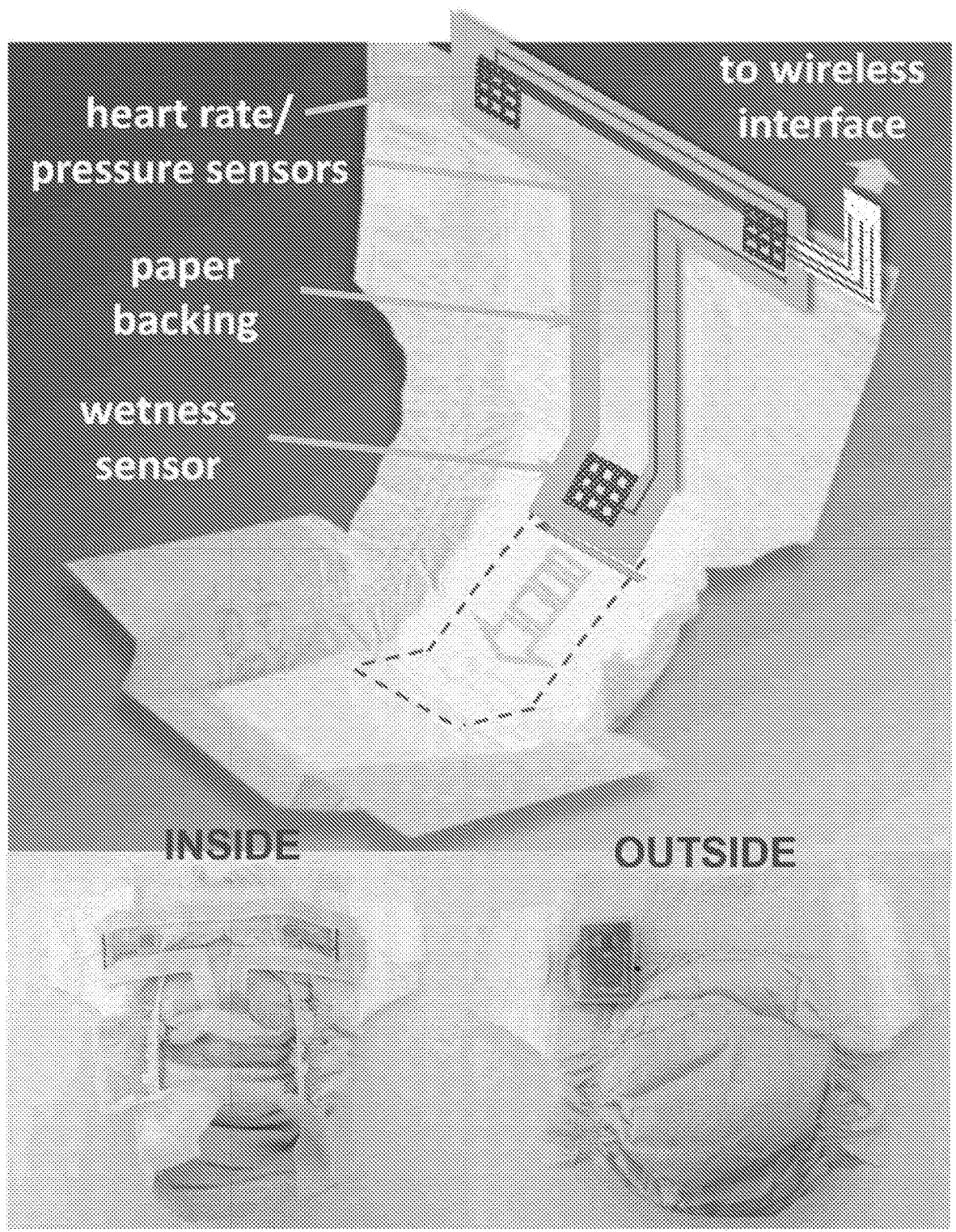
FIG. 24 is a pictorial representation of a paper sensor assembly shown incorporated into a diaper.

To implement the sensors into a wearable format, the sensors were attached onto a precut T-shaped backing made from ITW Texwipe Cleanroom Paper (FIG. 24). The paper backing contains traces to route sensor outputs to the interface circuits.

Three 16-texel paper-based sensor arrays were mounted onto the paper backing using an adhesive tape (3M Scotch) to provide relevant distributed sensing information from various locations throughout the diaper (FIG. 24). One of these sensor arrays was mounted at the bottom of the T-shape and was used primarily for wetness detection. The bottom of the T-shaped system was inserted through a slit in the diaper so that the wetness sensors were located within the diaper and were not in direct contact with the skin. The other two sensor arrays were mounted at the top of the T-shaped system and each was used for multimodal detection of ECG and pressure. This upper part of the T-shaped system wrapped around the waist portion of the diaper. Slits were cut in the diaper so that the ECG sensing texels maintain contact with the skin, whereas the pressure sensing texels were insulated from the skin by the diaper. FIG. 24 shows a complete diaper sensing system with the sensors and circuit mounted on the diaper.

For proof-of-concept, validation studies were conducted to assess the performance of the paper based sensors to detect pressure, wetness, and biopotentials. The diaper system was connected to the wireless circuit board interface and the change in sensor response to the conditions being applied (FIG. 25) was evaluated. For initial characterization of force sensing, calibration weights were used. The weights were applied over the entire patch of the 16-texel array and the change in the response was detected. For respiratory rate detections, the diaper system was worn by an adult subject. Ability to capture biopotential was evaluated by incorporating three sensing stripes (two for differential signal, one for reference) into two patches on each side of the waist worn by the subject. Wetness detection was characterized by applying drops of saline solution onto the texel and performing impedance spectroscopy in a dry scenario, immediately after solution application, and at time intervals following solution application.

In order to determine the appropriate impedance range for a given frequency, an LCR meter (Instek LCR-819) was used for calibration of the system. Once these parameters were identified, the AD5933 was programmed to work in the appropriate frequency and impedance range for more accurate adapted sensing.

Figure 25:
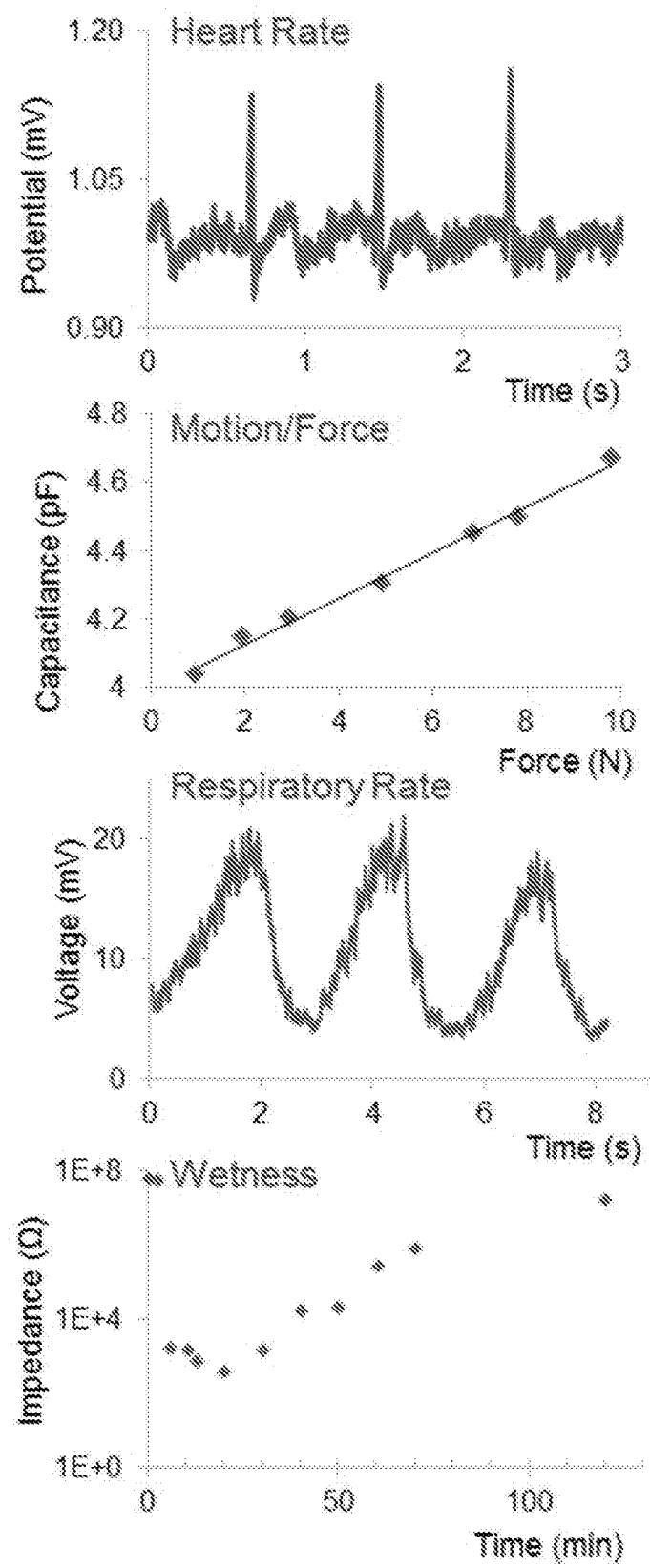
FIG. 25 is a graphical illustration of parameters from different sensors.

The capability of the paper-based sensors to measure biopotentials at the waist is shown in FIG. 25. The graph shows the typical ECG R peaks as well as indications of Q and T waves. In FIG. 25, the response of the paper sensors to application of force was shown to be linear. The respiratory modulation in the force sensor was observed through the capacitive divider followed by an envelope detector where the subject was asked to breathe with a period of 2 to 3 sec. (FIG. 25). Wetness detection capabilities were determined to be possible by analyzing the impedance between two layers at 1 kHz (FIG. 25) Immediately after applying the solution, the impedance decreased substantially, and after 20 minutes, the paper had absorbed all of the applied solution and the impedance decreased to less than 400Ω. After two hours of drying, the impedance had increased to levels close to that of the dry sensor in air (FIG. 25).

Various features and advantages of the invention are set forth in the following claims.

What is claimed is:

1. A sensing system comprising:
   a plurality of first multi-component strands, each of the first multi-component strands including an elongated conductive first portion and a plurality of elongated non-conductive portions positioned around the conductive first portion and extending along a length of the conductive first portion, wherein the elongated conductive first portion and the plurality of elongated non-conductive portions form an H configuration when viewed in cross-section;
   a plurality of second multi-component strands interwoven with the first multi-component strands, each of the second multi-component strands including an elongated conductive second portion and a plurality of elongated non-conductive portions positioned around the conductive second portion and extending along a length of the conductive second portion; and a plurality of third multi-component strands interwoven with the first multi-component strands and interwoven with the second multi-component strands, each of the third multi-component strands including an elongated conductive third portion and a plurality of elongated non-conductive portions positioned around the conductive third portion and extending along a length of the conductive third portion, the third multi-component strands being different than the first multi-component strands and the second multi-component strands;

wherein the second multi-component strands are oriented orthogonal relative to the first multi-component strands, and wherein the third multi-component strands are oriented orthogonal relative to the first multi-component strands and wherein a plurality of first texels are formed at an intersection where the non-conductive portions of the first multi-component strands and the non-conductive portion of the second multi-component strands are in contact and forming an air gap between the conductive first portion and the conductive second portion, and wherein a plurality of second texels are formed at an intersection where the non-conductive portions of the third multi-component strands and the non-conductive portions of the first multi-component strands are in contact and forming an air gap between the conductive first portion and the conductive third portion; and a circuit electrically coupled to the first texels and the second texels, the circuit configured to concurrently detect a change in capacitance or a change in impedance at the first texels and a biopotential signal of the user at the second texels.

2. The sensing system of claim 1, wherein the conductive portion of the first multi-component strands, the second multicomponent strands, and the third multi-component strands comprises polymeric, metallic, or polymer/metallic materials.

3. The sensing system of claim 1, wherein the non-conductive portion of the first multi-component strands, the second multicomponent strands, and the third multi-component strands comprises polymeric material.

4. The sensing system of claim 1, wherein the circuit further comprises a wireless communications circuit configured to wirelessly transmit data from the first texels and the second texels to a remote computing device.

5. The sensing system of claim 1, wherein the change in capacitance determines whether a force is applied to the first texels.

6. The sensing system of claim 1, wherein the change in impedance determines whether a fluid is applied to the first texels.

7. The sensing system of claim 1, wherein the biopotential is an electrocardiogram (ECG) signal.

8. A sensor patch comprising:
a first sensor formed at a first intersection of a first multi-component strand and a second multi-component strand, wherein the first multi-component strand forms an H configuration including a conductive first portion, a first insulator coupled to and orthogonally oriented relative to a first side of the conductive first portion and a second insulator coupled to and orthogonally oriented relative to a second side of the conductive first portion opposite the first side of the conductive first portion, the second multi-component strand includes a conductive second portion surrounded by a plurality of individual insulators, and wherein the first intersection includes an air gap separating the conductive first portion from the conductive second portion;

a second sensor formed at a second intersection of a third multi-component strand and the first multi-component strand, wherein the third multi-component strand includes a conductive third portion surrounded by a plurality of individual insulators, and wherein the second intersection includes an air gap separating the conductive first portion from the conductive third portion; and a circuit electrically coupled to the first sensor to detect a change in capacitance and a change in impedance, the circuit electrically coupled to the second sensor to detect a biopotential from a user.

9. The sensor patch of claim 8, wherein the circuit further comprises a wireless communications circuit configured to wirelessly transmit data from the first sensor and the second sensor to a remote computing device.

10. A sensor patch comprising:
a plurality of first multi-component strands, each of the first multi-component strands having an H configuration formed by a conductive portion and two non-conductive portions;
a plurality of second multi-component strands;
a plurality of third multi-component strands;
a first texel formed at a first intersection of the two non-conductive portions of one of the first multi-component strands and a non-conductive portion of one of the second multi-component strands, wherein the two non-conductive portions of the first multi-component strand and the non-conductive portion of the second multi-component strand forms a first air gap at the first intersection;
a second texel formed at a second intersection of the two non-conductive portions of one of the first multi-component strands and a non-conductive portion of one of the second multi-component strands, wherein the two non-conductive portions of the first multi-component strand and the non-conductive portion of the second multi-component strand forms a second air gap at the second intersection; and
a third texel formed at a third intersection of the two non-conductive portions of one of the first multi-component strands and a non-conductive portion of one of the third multi-component strands, wherein the two non-conductive portions of the first multi-component strand and the non-conductive portion of the third multi-component strand forms a third air gap at the third intersection,
wherein the first texel is configured to detect presence of fluid, the second texel is configured to detect an applied force, and the third texel is configured to detect a biopotential.

11. The sensor patch of claim 10, further comprising a circuit electrically coupled to the first texel to detect a change in impedance, to the second texel to detect a change in capacitance, and to the third texel to detect the biopotential from a user.

12. The sensor patch of claim 10, wherein the circuit further comprises a wireless communications circuit configured to wirelessly transmit data from the first texel, the second texel, and the third texel to a remote computing device.

13. The sensor patch of claim 10, wherein the first multi-component strands, the second multi-component strands, and the third multi-component strands include a conductive portion.

14. The sensor patch of claim 10, wherein the third multi-component strand is different than the first multi-component strand and the second multi-component strand.

15. The sensor patch of claim 10, wherein the first multi-component strand is different than the second multi-component strand.

16. A flexible array of sensors comprising:
- a first layer including a plurality of first multi-component strands interlaced with a plurality of second multi-component strands, at least one of the plurality of the first multi-component strands having an H configuration formed by a conductive portion and a plurality of entirely non-conductive portions positioned on opposite sides of the conductive portion;
- a second layer including a plurality of third multi-component strands interlaced with the first multi-component strands;
- a plurality of first sensors formed in the first layer at first air gaps due to contact between the non-conductive portions of the first multi-component strands and a non-conductive portion of the second multi-component strands, the first sensors configured to detect a change in capacitance;
- a plurality of second sensors formed in the first layer at second air gaps due to contact between the non-conductive portions of the first multi-component strands and the non-conductive portion of the second multi-component strands, the second sensors configured to detect a change in impedance; and
- a plurality of third sensors formed in the second layer at third air gaps due to contact between the non-conductive portions of the first multi-component strands and a non-conductive portion of the third multi-component strands, the third sensors configured to detect a signal.

17. The flexible array of sensors of claim 16, wherein the plurality of first sensors, the plurality of second sensors, and the plurality of third sensors are connectable to a circuit to provide an output of the capacitance, the impedance, and the signal, respectively.

* * * * *